US010668446B2

(12) United States Patent
Foley et al.

(10) Patent No.: US 10,668,446 B2
(45) Date of Patent: Jun. 2, 2020

(54) FLOW-THROUGH REACTORS FOR THE CONTINUOUS QUENCHING OF PEROXIDE MIXTURES AND METHODS COMPRISING THE SAME

(71) Applicant: P2 SCIENCE, INC., Woodbridge, CT (US)

(72) Inventors: Patrick Foley, New Haven, CT (US); Alexandre Chapeaux, New Haven, CT (US); Antonio Milicia, Milan (IT); Icilio Adami, Milan (IT)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 16/081,819

(22) PCT Filed: Jun. 21, 2017

(86) PCT No.: PCT/US2017/038577
§ 371 (c)(1),
(2) Date: Aug. 31, 2018

(87) PCT Pub. No.: WO2017/223220
PCT Pub. Date: Dec. 28, 2017

(65) Prior Publication Data
US 2019/0091645 A1    Mar. 28, 2019

Related U.S. Application Data

(60) Provisional application No. 62/504,487, filed on May 10, 2017, provisional application No. 62/352,926, filed on Jun. 21, 2016.

(51) Int. Cl.
*B01J 10/00* (2006.01)
*B01J 19/24* (2006.01)
(Continued)

(52) U.S. Cl.
CPC .......... *B01J 19/2415* (2013.01); *B01J 10/00* (2013.01); *B01J 10/007* (2013.01);
(Continued)

(58) Field of Classification Search
CPC .. B01J 19/242; B01J 19/2435; B01J 19/2415; B01J 19/2425; B01J 19/002;
(Continued)

(56) References Cited

U.S. PATENT DOCUMENTS 2,813,113 A    11/1957   Goebel et al.
3,023,244 A    2/1962    Eschinasi
(Continued)

FOREIGN PATENT DOCUMENTS

CA    1144561        4/1983
CA    2247662 A1     3/1999
(Continued)

OTHER PUBLICATIONS

Machine Translation of EP 2 404 666 (Year: 2012).*
(Continued)

*Primary Examiner* — Lessanework Seifu
(74) *Attorney, Agent, or Firm* — Hoxie & Associates LLC

(57) ABSTRACT

This disclosure relates to a highly efficient and safe reactor for the continuous quenching of peroxide mixtures generated during the reaction of unsaturated compounds with ozone, which minimizes the amount of highly reactive peroxides accumulated in the reactor at any given time. The reactor may be modified to allow for expansion to accommodate the quenching parameters of a wide variety of ozonolysis reactions and flow rates. The reactor may be constructed from highly pressure rated stainless steel for maximum durability, safety, and economic practicality while increasing the safety of peroxide quenching, thus allowing (Continued)

tighter process control and improved product yields. This disclosure also related to methods for quenching ozonides.

18 Claims, 16 Drawing Sheets

(51) Int. Cl.

| | |
|---|---|
| C07C 51/373 | (2006.01) |
| C07C 45/40 | (2006.01) |
| B01J 19/00 | (2006.01) |
| C07C 51/34 | (2006.01) |
| C07D 493/18 | (2006.01) |

(52) U.S. Cl.
CPC ....... B01J 19/0013 (2013.01); B01J 19/0093 (2013.01); B01J 19/242 (2013.01); B01J 19/243 (2013.01); B01J 19/2465 (2013.01); C07C 45/40 (2013.01); C07C 51/34 (2013.01); C07C 51/373 (2013.01); C07D 493/18 (2013.01); B01J 2219/0086 (2013.01); B01J 2219/00096 (2013.01); B01J 2219/00792 (2013.01); B01J 2219/00795 (2013.01); B01J 2219/00822 (2013.01); B01J 2219/00835 (2013.01); B01J 2219/00867 (2013.01); B01J 2219/00873 (2013.01); B01J 2219/00889 (2013.01)

(58) Field of Classification Search
CPC ........ B01J 19/0013; B01J 3/042; B01J 3/044; B01J 2219/00096; B01J 2219/00094; B01J 2219/00087; B01J 2219/0086
See application file for complete search history.

(56) References Cited

U.S. PATENT DOCUMENTS

| | | | |
|---|---|---|---|
| 3,699,169 | A | 10/1972 | Bertele et al. |
| 4,296,258 | A | 10/1981 | Fehr et al. |
| 4,311,617 | A | 1/1982 | Ansari et al. |
| 4,491,537 | A | 1/1985 | Futoshi et al. |
| 4,791,228 | A | 12/1988 | Siclari et al. |
| 4,940,808 | A | 7/1990 | Schulz et al. |
| 5,292,941 | A | 3/1994 | Kigawa et al. |
| 5,543,565 | A | 8/1996 | McVay et al. |
| 5,650,536 | A * | 7/1997 | Dankworth ............. C07C 67/38 560/193 |
| 5,756,821 | A | 5/1998 | Dilk et al. |
| 5,801,275 | A | 9/1998 | McVay et al. |
| 6,309,521 | B1 | 10/2001 | Andrews et al. |
| 6,395,695 | B1 | 5/2002 | Sivik |
| 6,512,131 | B1 | 1/2003 | Best et al. |
| 6,545,186 | B2 | 4/2003 | Giselbrecht et al. |
| 6,548,715 | B1 | 4/2003 | Bouillion et al. |
| 7,825,277 | B2 | 11/2010 | Gutsche et al. |
| 7,968,742 | B2 | 6/2011 | Aigner et al. |
| 8,221,708 | B2 | 7/2012 | Seebauer et al. |
| 9,035,091 | B2 | 5/2015 | Foley et al. |
| 9,604,898 | B2 | 3/2017 | Foley et al. |
| 9,682,914 | B2 | 6/2017 | Foley et al. |
| 9,701,606 | B2 | 7/2017 | Goeke et al. |
| 10,011,582 | B2 | 7/2018 | Foley et al. |
| 10,071,944 | B2 | 9/2018 | Foley et al. |
| 10,280,131 | B2 | 5/2019 | Foley et al. |
| 2003/0078453 | A1 | 4/2003 | Springer et al. |
| 2003/0100781 | A1 | 5/2003 | Springer et al. |
| 2004/0186042 | A1 | 9/2004 | Schmaus et al. |
| 2007/0010688 | A1 | 1/2007 | Ko et al. |
| 2007/0142666 | A1 | 6/2007 | Himeno et al. |
| 2007/0276165 | A1 | 11/2007 | Gutsche et al. |
| 2009/0221083 | A1 | 9/2009 | White et al. |
| 2013/0078685 | A1 | 3/2013 | Ulrich et al. |
| 2013/0177497 | A1 | 7/2013 | Fitch et al. |
| 2013/0338150 | A1 | 12/2013 | Boehme et al. |
| 2014/0031584 | A1* | 1/2014 | Foley ................ C07C 51/34 562/524 |
| 2014/0316149 | A1 | 10/2014 | Wickens et al. |
| 2015/0183707 | A1* | 7/2015 | Foley ................ C07C 51/34 562/524 |
| 2017/0247314 | A1 | 8/2017 | Foley et al. |
| 2017/0275230 | A1 | 9/2017 | Foley et al. |

FOREIGN PATENT DOCUMENTS

| | | |
|---|---|---|
| CN | 102653531 A | 9/2012 |
| CN | 102795987 A | 11/2012 |
| EP | 0761629 A1 | 3/1997 |
| EP | 2 404 666 * | 11/2012 |
| JP | H06-135878 | 5/1994 |
| WO | WO 1993/002991 | 2/1993 |
| WO | WO 1995/001960 | 1/1995 |
| WO | WO 2002/048431 | 6/2002 |
| WO | WO 2007/068498 | 6/2007 |
| WO | WO 2009/061806 | 5/2009 |
| WO | WO 2012/177357 | 12/2012 |
| WO | WO 2013/053102 | 4/2013 |
| WO | WO 2013/053787 A1 | 4/2013 |
| WO | WO 2015/039010 | 3/2015 |
| WO | WO 2015/106293 | 7/2015 |
| WO | WO 2015/126936 | 8/2015 |
| WO | WO 2015/191706 | 12/2015 |
| WO | WO 2015/196019 | 12/2015 |
| WO | WO 2016/091895 | 6/2016 |
| WO | WO 2017/223220 | 12/2017 |
| WO | WO 2018/053289 | 3/2018 |

OTHER PUBLICATIONS

Written Opinion of the International Searching Authority for International Application No. PCT/US2017/051817 dated Dec. 8, 2017, 9 pages.
English Abstract of Japanese Publication No. H06-135878, published May 17, 1994.
Abe, et al, "Synthesis of Massoia lactone and its analogs. I. Synthesis of the lactone of 1-decen-4-ol-1-carboxylic acid," 75 Nippon Kagaka Kaishi, Pure Chem., 953-5, (1921-1947), (1954). [CAS Abstract Only].
Avdeev, et al., "Molecular Mechanism of Oxygen Isotopic Exchange over Supported Vanadium Oxide Catalyst Vox/TiO2," *The Journal of Physical Chemistry C*, vol. 117, No. 6, pp. 2879-2887, (2013).
Ayer, et al., "Degraded Monoterpenes from the Opisthobranch Mollusc *Melibe Leonina*," Short Communications, Experientia 39, Birkhauser Verlag, CH-4010 Basel/Switzerland, (1983), 2 pages.
Cahn, "An Introduction to the Sequence Rule. A System for the Specification of Absolute Configuration," *Journal of Chemical Education*, vol. 41, No. 3, pp. 116-125, (1964).
Cahn, et al., "The Specification of Asymmetric Configuration in Organic Chemistry," *Experientia*, vol. 12, pp. 81-94, (1956).
Cahn, et al., "Specification of Configuration about Quadricovalent Asymmetric Atoms," *J. Chem. Soc.*, pp. 612-622, (1951).
Cahn, et al., "Specification of Molecular Chirality," *Angew. Chem. Inter. Edit.*, vol. 5, No. 4, pp. 385-415, (1966).
Cermak, et al., "Synthesis of δ-Stearolactone from Oleic Acid," *JAOCS*, vol. 77, No. 3, pp. 243-248, (2000).
Chen, et al., "A Predictably Selective Aliphatic C—H Oxidation Reaction for Complex Molecule Synthesis," *Science*, vol. 318, (2007).
Chmielewski, et al., "Organic Syntheses Under High Pressure. 3. General Approach to the Synthesis of Naturally Occuring .delta.-lactones," *The Journal of Organic Chemistry*, vol. 46, No. 11, pp. 2230-2233, (1981).
"Aliphatic Carboxylic Acids," Competition Science Vision Aug. 2000, *Pratiyogita Darpan*, vol. 3, No. 30, pp. 799. [ 2 pages].
Cook, et al., "Study of the Total Synthesis of (—)—Exiguolide," *J. Org. Chem.*, vol. 77, pp. 6728-6742, (2012).
Cullen, William, "Re: Melibe from Alaska," Jan. 12, 2001, Australian Museum, Sydney, pp. 1-4.

(56) References Cited

OTHER PUBLICATIONS

Dupe, et al., "Methyl Ricinoleate as Platform Chemical for Simultaneous Production of Fine Chemicals and Polymer Precursors," *ChemSusChem.*, vol. 5, pp. 2249-2254, (2012).
Förtsch, et al., "Synthese, Kristallstruktur und Reaktionen neuartiger metallacyclischer Dioxo— und Aminooxocarben-Komplexe des Eisens," *Chem. Ber.*, vol. 127, pp. 711-715, (1994). [English Abstract Only.].
Gerth, et al., "Synthesis of δ-Lactones via Radical C-C Bond Formation Using Chiral Radical Precursors," *J. Org. Chem.*, vol. 51, pp. 3726-3729, (1986).
Gross, R.A., Jr., "Ozonolysis Problems That Promote Student Reasoning," *Journal of Chemical Education*, vol. 83, No. 4, pp. 604-609, (2006).
Harding, et al., "beta-Methyl-delta-dodecadiene and beta-Methyl-delta-decadiene," *Journal of the Chemical Society*, Transactions, pp. 448-451, (1911).
Hearn, et al., "Kinetics and Product Studies for Ozonolysis Reactions of Organic Particles Using Aerosol CIMS," *The Journal of Physical Chemistry A*, vol. 108, No. 45, pp. 10019-10029, (2004).
Kadesch, R.G., "Ozonolysis of Fatty Acids and Their Derivatives," *Progress in the Chemistry of Fats and Other Lipids*, vol. 6, pp. 291-312, (1963).
Kauffmann, et al., "Ubergangsmetallaktivierte organische Verbindungen, XXXVIII. Chemoselektive nucleophile Methylierungen durch In-Situ-Blockierung von Aldehydgruppen unter [alpha]1-Phosphonioalkoxid-Bildung," *Chemishe Berichte*, pp. 459-464, (1993). [No English Translation.].
Kula, et al., "Synthesis of Enantiomerically Pure Volatile Compounds Derived From (R)-3-Hydroxynonanal," *Tetrahedron: Asymmetry*, vol. 11, pp. 943-950, (2000).
Lee, et al., "Tin-free, Radical-mediated Gamma-alkylations of Alpha, Beta-unsaturated Esters via O-tert-alkyl Dienol Ethers," vol. 1, pp. 49-54, (2008).
Maggiolo, A. "Ozonization of Fatty Acids and Their Derivatives," *The Journal of the American Oil Chemists' Society*, vol. 40, pp. 161-164, (1963).
Otsubo, et al., "A Direct Synthesis of [gamma]—, [delta], and [epsilon]— Lactones Utilizing SmI2-induced Barbier-type Reaction in the Presence of Hexamethylphosphoric Triamide (HMPA)," *Chemistry Letters*, pp. 1487-1490, (1987). Http://www.journal.csj.jp/doi/pdf/10.1246/c1.1987.1487 [retrieved on May 29, 2017].
PubChem-CID-107500001, Oct. 26, 2006, 17 pages.
Quan, et al., "A Convenient Protecting Group for Aldehydes," *Synlett*, vol. 2001, No. 12, pp. 1925-1926, (2001).
Rani, et al., "Ozonolysis of Oleic Acid Over a Nano Vanadium Pentoxide (V2O5) Catalyst," *European Journal of Scientific Research*, vol. 24, No. 3, pp. 428-432, (2008).
Richardson, et al., "A Practical Synthesis of Long-Chain Iso-Fatty Acids (iso-C12-C19) and Related Natural Products," *Beilstein Journal of Organic Chemistry*, vol. 9, pp. 1807-1812, (2013).
Rosenberger, et al., "28. Synthesis of δ-Lactones From Glutaraldehyde," *Helvetica Chimica Acta*, vol. 55, pp. 249-255, (1972).
Sabitha, et al., "The First Asymmetric Total Synthesis of (R)-Tuberolactone, (S)-Jasmine Lactone, and (R)-δ-Decalactone," *Tetrahedron Letters*, vol. 47, pp. 8179-8181, (2006).
Schiaffo, C.E., "I. An Improved Procedure for Alkene Ozonolysis. II. Exploring a New Structural Paradigm for Peroxide Antimalarials," *Student Research Projects, Dissertations, and Theses—Chemistry, Department, University of Nebraska-Lincoln*, (Jun. 2011), Paper 23.
Shao, et al., "Asymmetric Hydrogenation of 3,5-Dioxoesters Catalyzed by Ru-binap Complex: A Short Step Asymmetric Synthesis of 6-Substituted 5,6-dihyrdo-2-pyrones," *Tetrahedron*, vol. 49, No. 10, pp. 1997-2010, (1993).
Shekhter, et al., "Study of Compounds with Juvenile-hormone Activity. X. Synthesis of Esters of 2E,4E-3,11-dimethyl-11-methoxy-2,4-dodecadienic and 2E,4E-2, 11-dimethyl-2,4,10-dodecatrienic acids," *Zhurnal Organicheskoi Khimii*, vol. 15, No. 2, pp. 260-264, (1979).
Shono, et al., "Electroreductive Intermolecular Coupling of Ketones with Olefins," *J. Org. Chem.*, vol. 54, No. 26, pp. 6001-6003, (1989).
STN 1984 (Year: 1984), p. 1.
STN Nov. 1984 (Year: 1984), 1 Page.
STN 1995 (Year: 1995), 1 Page.
STN Sep. 29, 2005 (Year: 2005), 1 Page.
STN Mar. 7, 2013 (Year: 2013), 1 Page.
Surburg, et al., *Common Fragrance and Flavor Materials*, 5th Ed. Wiley-VCH, pp. 149-172, (2006).
Tanaka, et al., "Syntheses of (5E)-PGE2 and New 6-Functionalized Derivatives By the Use of Palladium-Catalyzed Decarboxylative Allylic Alkylation," *Tetrahedron*, vol. 42, No. 24, pp. 6747-6758, (1986).
Utaka, et al., "New Synthesis of Jasmine Lactone and Related-δ-Lactones from 1,2 Cyclohexanedione. Preparation and Dye-Sensitized Photooxygenation of 3-(2-Alkenyl)-and 3-(2-Alkynyl)-1,2-cyclohexanediones," *J. Org. Chem.*, vol. 51, No. 6, pp. 935-938, (1986).
Wasmi, et al, "Synthesis of Vanadium Pentoxide Nanoparticles as Catalysts for the Ozonation of Palm Oil," *Ozone: Science & Engineering*, vol. 38, No. 1, pp. 36-41, (2015).
Willand-Charnley, et al., "Pyridine is an Organocatalyst for the Reactive Ozonolysis of Alkenes," *Org. Lett.*, vol. 14, No. 9, pp. 2242-2245, (2012).
Yahata, et al., "Methodology for in Situ Protection of Aldehydes and Ketones Using Trimethylsilyl Trifluoromethanesulfonate and Phosphines: Selective Alkylation and Reduction of Ketones, Esters, Amides, and Nitriles," *Chem. Pharm. Bull.*, vol. 61, No. 12, pp. 1298-1307.
Omonov, et al., "The Production of Biobased Nonanal by Ozonolysis of Fatty Acids," *RSC Adv.*, vol. 4, pp. 53617-53627, (2014); DOI: 10.1039/c4ra07917e.

* cited by examiner

FLOW-THROUGH REACTORS FOR THE CONTINUOUS QUENCHING OF PEROXIDE MIXTURES AND METHODS COMPRISING THE SAME

CROSS-REFERENCE TO RELATED APPLICATIONS

This application is a U.S. National Stage application filed under 35 U.S.C. § 371 of International Application No. PCT/US2017/038577, filed Jun. 21, 2017, which claims the benefit of and priority to U.S. Provisional Application No. 62/352,926, filed Jun. 21, 2016, and U.S. Provisional Application No. 62/504,487, filed May 10, 2017, the entire contents of each of which are incorporated herein by reference.

TECHNICAL FIELD

The present disclosure relates generally to systems and methods for the continuous quenching of peroxide mixtures. More specifically, the present disclosure relates to continuous flow reactors for the continuous quenching of peroxide mixtures generated from the ozonolysis of an unsaturated organic compound. Additionally, the present disclosure relates to methods of quenching ozonides.

BACKGROUND

Ozonolysis is an extremely useful transformation in organic chemistry that allows one to access alcohol, aldehyde, and/or carboxylic acid functionality from the oxidative cleavage of unsaturated compounds. This reaction is very exothermic and the peroxide intermediates, i.e., ozonides, that are generated can be very unstable and potentially explosive. Further, the reaction is often done in the presence of a highly oxygenated atmosphere, which makes it all the more necessary to control heat. For this reason much research has gone into optimizing the process control and safety of the ozonolysis reaction.

Previous examples of reactors attempt to address the problem of continuous quenching of peroxide mixtures (PM) by scaling the process down into microchannels. This approach fails to allow for scale-up as it is not capital efficient to add multiple reactors in series, and it adds considerable complexity to the process. Further, the residence time of the reactive peroxide mixtures (PM) in the microchannels is not well controlled given the non-adjustable nature of the microchannels, thus adding complexity to this type of reactor across multiple quenching chemistries.

This complexity is further compiled by the fact that the ozonides may have very different stabilities, ranging from highly unstable to highly stable. Therefore, ozonides may have very different processing requirements depending upon their relative stabilities. Indeed, some ozonides are so stable that effective quenching methods have not yet been identified and thus yields from the corresponding quenching reaction are not ideal. As such, there is a need for the discovery and development of new methods for processing such ozonides.

SUMMARY

There remains a need to handle the peroxide mixtures (PM) in the peroxide quenching reaction. For example, the importance of the reactor design and its adjustability is underscored by the nature of the quenching reaction itself, which can be performed by a number of different reagents, but all of them will release a significant amount of heat upon reaction with peroxide mixtures. This may potentially result in the peroxide mixtures being heated, thus leading to increased reactivity of the peroxide mixtures, which leads to further unwanted side reactions and further heating of peroxide mixtures, i.e., a run-away event. This could potentially lead to damage to the reactor itself and safety concerns due to possible explosions.

The present disclosure addresses all of these design considerations by using a flow-through reactor for the continuous quenching of a peroxide mixture (PM).

The reactor is designed to minimize the concentration of peroxide mixtures (including ozonides) accumulated following ozonolysis by reacting the peroxide mixtures (PM) at a rate that is synchronized with the continuous ozonolysis operation. Optionally, the reactor for the continuous quenching of peroxide mixtures (PM) may be expanded/contracted by adding/removing additional piping from/to the reactor through a series of valves that in turn allows for adjustment of the residence time, i.e., time spent in the reactor, of the peroxide mixtures (PM) and peroxide quenching solutions (PQS). The reactor may be constructed using stainless steel or metal-alloy piping of a small enough dimension that would allow for optimal heat removal, while also having a thickness that would provide a pressure rating such that should a run-away event occur, it would be fully contained. For all of these reasons, the flow-through reactor for the continuous quenching of a peroxide mixture (PM) described herein has clear advantages over previously disclosed reactors in terms of safety, scalability, simplicity, and cost. For example, the flow-through reactor for the continuous quenching of a peroxide mixture (PM) may be expanded or contracted based on the demands of the specific chemistry being conducted. As a result, the reactor will contain only as much of the peroxide mixture (PM) and/or peroxide quenching solution (QPS) as is required at any given time, further optimizing the safety of the system. These features cannot be easily accomplished with incumbent reactor designs.

Provided herein is a single-pass flow-through reactor for the continuous quenching of a peroxide mixture (PM), said reactor comprising:

a single input for both a peroxide mixture (PM) and a peroxide quenching solution (PQS);

an output for a quenched product solution (QPS); and optionally, a circulatory pump (CP), a heat exchanger (HE), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

For example, the reactor further comprises:

a second single-pass flow-through reactor connected to the first single-pass flow-through reactor, said second reactor optionally comprising a circulatory pump (CP), heat exchanger (HE), or both;

wherein the flow in the reactor has a flow rate, F, the input for the peroxide mixture (PM) and peroxide quenching solution (PQS) has a flow rate into the first reactor, $F_{in}$, and the output for the quenched product solution (QPS) has a flow rate out of the second reactor, $F_{out}$.

For example, the reactor further comprises:

n additional single-pass flow-through reactors connected in series to the first single-pass flow-through reactor, wherein each additional reactor optionally comprises a circulatory pump (CP), heat exchanger (HE), or both;

wherein the flow in the reactor has a flow rate, F, the input for the peroxide mixture (PM) and peroxide quenching solution (PQS) has a flow rate into the first reactor, $F_{in}$, and the output for the quenched product solution (QPS) has a flow rate out of the last reactor, $F_{out}$;

wherein n is an integer greater than or equal to 2.

For example, n is an integer from 2 to 50.

Provided herein is a single-pass flow-through reactor for the continuous quenching of a peroxide mixture (PM), said reactor comprising:

a first input for a peroxide mixture (PM);

a second input for a peroxide quenching solution (PQS);

an output for a quenched product solution (QPS); and, optionally, a circulatory pump (CP), a heat exchanger (HE), or both;

wherein the flow in the reactor has a flow rate, F, the first input for the peroxide mixture (PM) has a flow rate into the reactor, $F'_{in}$, the second input for the peroxide quenching solution (PQS) has a flow rate into the reactor, $F''_{in}$, and the output for the quenched product solution (QPS) has a flow rate out of the reactor, $F_{out}$.

For example, the reactor further comprises:

a second single-pass flow-through reactor connected to the first single-pass flow-through reactor, said second reactor optionally comprising a circulatory pump (CP), heat exchanger (HE), or both;

wherein the flow in the reactor has a flow rate, F, the first input for the peroxide mixture (PM) has a flow rate into the first reactor, $F'_{in}$, the second input for the peroxide quenching solution (PQS) has a flow rate into the first reactor, $F''_{in}$, and the output for the quenched product solution (QPS) has a flow rate out of the second reactor, $F_{out}$.

For example, wherein the reactor further comprises:

n additional single-pass flow-through reactors connected in series to the first single-pass flow-through reactor, wherein each additional reactor optionally comprises a circulatory pump (CP), heat exchanger (HE), or both;

wherein the flow in the reactor has a flow rate, F, the first input for the peroxide mixture (PM) has a flow rate into the first reactor, $F'_{in}$, the second input for the peroxide quenching solution (PQS) has a flow rate into the first reactor, $F''_{in}$, and the output for the quenched product solution (QPS) has a flow rate out of the last reactor, $F_{out}$;

wherein n is an integer greater than or equal to 2.

For example, n is an integer from 2 to 50.

For example, the overall peroxide concentration in the peroxide mixture (PM) prior to entering the reactor is 500-2000 mmol/L as determined by iodometric titration.

For example, the overall peroxide concentration in the quenched product solution (QPS) upon exiting the reactor is less than or equal to 100 mmol/L as determined by iodometric titration.

For example, each reactor independently has a diameter of 0.25 inches to 10 inches, 0.5 inches to 8 inches, or 1 inch to 6 inches.

For example, each reactor independently has a length of 5 m to 200 m, 7.5 m to 150 m, or 10 m to 100 m.

For example, the peroxide mixture (PM) has a residence time in the reactor from 1 to 200 minutes or 5 to 120 minutes.

For example, each heat exchanger (HE) independently maintains the temperature in the reactor at −78° C. to 300° C., −40° C. to 150° C., −25° C. to 29° C., 0° C. to 100° C., 0° C. to 29° C., 20° C. to 100° C., 20° C. to 80° C., 20° C. to 60° C., 60° C. to 80° C., or 80° C. to 110° C.

For example, the heat exchanger can be a brazed plate heat exchanger, an fusion-bonded plate heat exchanger, an gasketed plate-and-frame heat exchanger, an welded plate-and-shell heat exchanger, an welded plate-and-block heat exchanger, a printed circuit heat exchanger, a welded spiral heat exchanger, or a welded plate-and-frame heat exchanger.

For example, the heat exchanger is an Alfa Laval brazed plate heat exchanger, an Alfa Laval fusion-bonded plate heat exchanger, an Alfa Laval gasketed plate-and-frame heat exchanger, an Alfa Laval welded plate-and-shell heat exchanger, an Alfa Laval welded plate-and-block heat exchanger, an Alfa Laval printed circuit heat exchanger, an Alfa Laval welded spiral heat exchanger, or an Alfa Laval welded plate-and-frame heat exchanger.

For example, the heat exchanger is an Alfa Laval gasketed plate-and-frame heat exchanger.

For example, the heat exchanger is the reactor.

For example, the output for the quenched product solution (QPS) has a flow rate out of the reactor, $F_{out}$, of 80 to about 1,000,000 mL/minute, 100 to about 500,000 mL/minute, 1,000 to about 100,000 mL/minute.

For example, the overall pressure in the reactor is 1 psi to 6000 psi, 1 psi to 2000 psi, 1 psi to 1000 psi, 1 psi to 500 psi, 1 psi to 200 psi, 1 psi to 100 psi, or 1 psi to 50 psi.

For example, the circulatory pump is an electrically-powered centrifugal pump.

For example, the reactor further comprises one or more static mixers.

For example, the reactor is made of marine grade stainless steel piping or nickel-alloy piping.

For example, the piping has Schedule 40 dimensions, Schedule 80 dimensions, or Schedule 160 dimensions.

For example, the peroxide quenching solution (PQS) quenches the peroxide mixture (PM) oxidatively.

For example, the peroxide quenching solution (PQS) comprises nitric acid.

For example, the peroxide quenching solution (PQS) quenches the peroxide mixture (PM) reductively.

For example, the peroxide quenching solution (PQS) comprises thiodiglycol.

For example, the peroxide mixture (PM) is derived from any $C_4$-$C_{50}$ unsaturated material.

For example, the peroxide mixture (PM) is derived from a terpene, fatty acid ester, fatty acid, or vegetable oil.

For example, the reactor is placed in line with an ozonolysis operation.

For example, the reactor is placed in line with a continuous ozonolysis operation from a tubular falling film reactor system with one or multiple tubes wherein the combined ozone and carrier gas flow is co-current.

Provided herein is a recirculating flow-through reactor for the continuous quenching of a peroxide mixture (PM), said reactor comprising:

a single input for both a peroxide mixture (PM) and a peroxide quenching solution (PQS);

an output for a quenched product solution (QPS);

optionally, a circulatory pump (CP), a heat exchanger (HE), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

For example, the flow rate of the peroxide mixture (PM) and peroxide quenching solution (PQS) into the reactor, $F_{in}$, is about equal to the flow rate of the quenched product solution (QPS) out of the reactor, $F_{out}$.

For example, the flow rate of the peroxide mixture (PM) and peroxide quenching solution (PQS) into the reactor, $F_{in}$, is equal to the flow rate of the quenched product solution (QPS) out of the reactor, $F_{out}$.

Provided herein is a recirculating flow-through reactor for the continuous quenching of a peroxide mixture (PM), said reactor comprising:
 a first input for a peroxide mixture (PM);
 a second input for a peroxide quenching solution (PQS);
 an output for a quenched product solution (QPS);
 optionally, a circulatory pump (CP), a heat exchanger (HE), or both;
 wherein the flow in the reactor has a flow rate, F, the first input for the peroxide mixture (PM) has a flow rate into the reactor, $F'_{in}$, the second input for the peroxide quenching solution (PQS) has a flow rate into the reactor, $F''_{in}$, and the output for the quenched product solution (QPS) has a flow rate out of the reactor, $F_{out}$.

For example, the sum of the flow rate of the peroxide mixture (PM) into the reactor, $F'_{in}$, and the flow rate of peroxide quenching solution (PQS) into the reactor, $F''_{in}$, is about equal to the flow rate of the quenched product solution (QPS) out of the reactor, $F_{out}$.

For example, the sum of the flow rate of the peroxide mixture (PM) into the reactor, $F'_{in}$, and the flow rate of peroxide quenching solution (PQS) into the reactor, $F''_{in}$, is equal to the flow rate of the quenched product solution (QPS) out of the reactor, $F_{out}$.

For example, the flow rate in the reactor, F, is greater than the flow rate of the quenched product solution (QPS) out of the reactor, $F_{out}$.

For example, the overall peroxide concentration in the peroxide mixture (PM) prior to entering the reactor is 500-2000 mmol/L as determined by iodometric titration.

For example, the overall peroxide concentration in the quenched product solution (QPS) upon exiting the reactor is less than or equal to 100 mmol/L as determined by iodometric titration.

For example, said reactor further comprises additional piping attached to said reactor through valves $V_1$ and $V'_1$, wherein $V_1$ is set to permit flow into the additional piping ($F_1$) and $V'_1$ is set to restrict flow back to $V_1$.

For example, the reactor further comprises additional piping attached to said reactor through valves $V_2$ and $V'_2$, wherein $V_2$ is set to permit flow into the additional piping ($F_2$) and $V'_2$ is set to restrict flow back to $V_2$.

For example, the reactor has a diameter of 0.25 inches to 10 inches.

For example, the reactor has a diameter of 0.5 inches to 8 inches.

For example, the reactor has a diameter of 1 inch to 6 inches.

For example, the reactor has a length of 5 m to 200 m.
For example, the reactor has a length of 7.5 m to 150 m.
For example, the reactor has a length of 10 m to 100 m.
For example, the peroxide mixture (PM) has a residence time in the reactor from 1 to 200 minutes.

For example, the peroxide mixture (PM) has a residence time in the reactor from 5 to 120 minutes.

For example, the heat exchanger (HE) maintains the temperature in the reactor at −78° C. to 300° C.

For example, the heat exchanger (HE) maintains the temperature in the reactor at −40° C. to 150° C.

For example, the heat exchanger (HE) maintains the temperature in the reactor at −25° C. to 29° C.

For example, the heat exchanger (HE) maintains the temperature in the reactor at 0° C. to 100° C.

For example, the heat exchanger (HE) maintains the temperature in the reactor at 0° C. to 29° C.

For example, the heat exchanger (HE) maintains the temperature in the reactor at 20° C. to 100° C.

For example, the heat exchanger (HE) maintains the temperature in the reactor at 20° C. to 80° C.

For example, the heat exchanger (HE) maintains the temperature in the reactor at 20° C. to 60° C.

For example, the heat exchanger can be a brazed plate heat exchanger, an fusion-bonded plate heat exchanger, an gasketed plate-and-frame heat exchanger, an welded plate-and-shell heat exchanger, an welded plate-and-block heat exchanger, a printed circuit heat exchanger, a welded spiral heat exchanger, or a welded plate-and-frame heat exchanger.

For example, the heat exchanger is an Alfa Laval brazed plate heat exchanger, an Alfa Laval fusion-bonded plate heat exchanger, an Alfa Laval gasketed plate-and-frame heat exchanger, an Alfa Laval welded plate-and-shell heat exchanger, an Alfa Laval welded plate-and-block heat exchanger, an Alfa Laval printed circuit heat exchanger, an Alfa Laval welded spiral heat exchanger, or an Alfa Laval welded plate-and-frame heat exchanger.

For example, the heat exchanger is an Alfa Laval gasketed plate-and-frame heat exchanger.

For example, the heat exchanger is the reactor.

For example, the output for the quenched product solution (QPS) has a flow rate out of the reactor, $F_{out}$, of 80 to about 1,000,000 mL/minute.

For example, the output for the quenched product solution (QPS) has a flow rate out of the reactor, $F_{out}$, of 100 to about 500,000 mL/minute.

For example, the output for the quenched product solution (QPS) has a flow rate out of the reactor, $F_{out}$, of about 1,000 to about 100,000 mL/minute.

For example, the overall pressure in the reactor is 1 psi to 6000 psi.

For example, the overall pressure in the reactor is 1 psi to 2000 psi.

For example, the overall pressure in the reactor is 1 psi to 1000 psi.

For example, the overall pressure in the reactor is 1 psi to 500 psi.

For example, the overall pressure in the reactor is 1 psi to 200 psi.

For example, the overall pressure in the reactor is 1 psi to 100 psi.

For example, the overall pressure in the reactor is 1 psi to 50 psi.

For example, the circulatory pump is an electrically powered centrifugal pump.

For example, the reactor further comprises one or more static mixers.

For example, the reactor is made of marine grade stainless steel piping.

For example, the reactor is made of nickel-alloy piping.
For example, the piping has Schedule 40 dimensions.
For example, the piping has Schedule 80 dimensions.
For example, the piping has Schedule 160 dimensions.
For example, the peroxide quenching solution (PQS) quenches the peroxide mixture (PM) oxidatively.

For example, the peroxide quenching solution (PQS) comprises nitric acid.

For example, the peroxide quenching solution (PQS) quenches the peroxide mixture (PM) reductively.

For example, the peroxide quenching solution (PQS) comprises thiodiglycol.

For example, the peroxide mixture (PM) is derived from any $C_4$-$C_{50}$ unsaturated material.

For example, the peroxide mixture (PM) is derived from a terpene.

For example, the peroxide mixture (PM) is derived from a fatty acid ester.

For example, the peroxide mixture (PM) is derived from a fatty acid.

For example, the peroxide mixture (PM) is derived from a vegetable oil.

For example, the reactor is placed in line with an ozonolysis operation.

For example, the reactor is placed in line with a continuous ozonolysis operation from a tubular falling film reactor system with one or multiple tubes wherein the combined ozone and carrier gas flow is co-current.

For example, the peroxide mixture (PM) and a peroxide quenching solution (PQS) are recirculated through the reactor at least once before collecting the quenched product solution (QPS) from the output.

Provided herein is a method of continuously quenching a peroxide mixture (PM) in a recirculating flow-through reactor, said reactor comprising:

a single input for both a peroxide mixture (PM) and a peroxide quenching solution (PQS);

an output for a quenched product solution (QPS);

optionally, a circulatory pump (CP), a heat exchanger (HE), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

Provided herein is a method of continuously quenching a peroxide mixture (PM) in a recirculating flow-through reactor, said reactor comprising:

a first input for a peroxide mixture (PM);

a second input for a peroxide quenching solution (PQS);

an output for a quenched product solution (QPS);

optionally, a circulatory pump (CP), a heat exchanger (HE), or both;

wherein the flow in the reactor has a flow rate, F, the first input for the peroxide mixture (PM) has a flow rate into the reactor, $F'_{in}$, the second input for the peroxide quenching solution (PQS) has a flow rate into the reactor, $F''_{in}$, and the output for the quenched product solution (QPS) has a flow rate out of the reactor, $F_{out}$.

For example, the peroxide mixture (PM) is derived from any $C_4$-$C_{50}$ unsaturated material.

For example, the peroxide mixture (PM) is derived from a terpene.

For example, the peroxide mixture (PM) is derived from a fatty acid ester.

For example, the peroxide mixture (PM) is derived from a fatty acid.

For example, the peroxide mixture (PM) is derived from a vegetable oil.

Provided herein is a method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) and a peroxide quenching solution (PQS) into a peroxide mixture (PM) and peroxide quenching solution (PQS) feeding chamber;

(e) feeding the peroxide mixture (PM) and peroxide quenching solution (PQS) into a recirculating flow-through reactor for the continuous quenching of the peroxide mixture (PM), said reactor comprising:

(i) a single input for both a peroxide mixture (PM) and a peroxide quenching solution (PQS);

(ii) an output for a quenched product solution (QPS);

(iii) optionally, a circulatory pump (CP), a heat exchanger (HE), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

Provided herein is a method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

(a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) into a recirculating flow-through reactor for the continuous quenching of the peroxide mixture (PM), said reactor comprising:

(i) a first input for a peroxide mixture (PM);

(ii) a second input for a peroxide quenching solution (PQS);

(iii) an output for a quenched product solution (QPS);

(iv) optionally, a circulatory pump (CP), a heat exchanger (HE), or both;

wherein the flow in the reactor has a flow rate, F, the first input for the peroxide mixture (PM) has a flow rate into the reactor, $F_{in}$, the second input for the peroxide quenching solution (PQS) has a flow rate into the reactor, $F''_{in}$, and the output for the quenched product solution (QPS) has a flow rate out of the reactor, $F_{out}$.

For example, the overall peroxide concentration in the peroxide mixture (PM) prior to entering the reactor is 500-2000 mmol/L as determined by iodometric titration.

For example, the overall peroxide concentration in the quenched product solution (QPS) upon exiting the reactor is less than or equal to 100 mmol/L as determined by iodometric titration.

For example, the overall peroxide concentration in the quenched product solution (QPS) upon exiting the reactor is about 100 mmol/L as determined by iodometric titration.

For example, the reactor has a diameter of 1 inch to 6 inches.

For example, the reactor has a length of 10 m to 100 m.

For example, the peroxide mixture (PM) has a residence time in the reactor from 1 to 200 minutes.

For example, the peroxide mixture (PM) has a residence time in the reactor from 5 to 120 minutes.

For example, the heat exchanger (HE) maintains the temperature in the reactor at −78° C. to 300° C.

For example, the heat exchanger (HE) maintains the temperature in the reactor at −40° C. to 150° C.

For example, the heat exchanger (HE) maintains the temperature in the reactor at −25° C. to 29° C.

For example, the heat exchanger (HE) maintains the temperature in the reactor at 0° C. to 100° C.

For example, the heat exchanger (HE) maintains the temperature in the reactor at 0° C. to 29° C.

For example, the heat exchanger (HE) maintains the temperature in the reactor at 20° C. to 100° C.

For example, the heat exchanger (HE) maintains the temperature in the reactor at 20° C. to 80° C.

For example, the heat exchanger (HE) maintains the temperature in the reactor at 20° C. to 60° C.

For example, the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or a welded plate-and-frame heat exchanger.

For example, the heat exchanger is an Alfa Laval brazed plate heat exchanger, an Alfa Laval fusion-bonded plate heat exchanger, an Alfa Laval gasketed plate-and-frame heat exchanger, an Alfa Laval welded plate-and-shell heat exchanger, an Alfa Laval welded plate-and-block heat exchanger, an Alfa Laval printed circuit heat exchanger, an Alfa Laval welded spiral heat exchanger, or an Alfa Laval welded plate-and-frame heat exchanger.

For example, the heat exchanger is an Alfa Laval gasketed plate-and-frame heat exchanger.

For example, the heat exchanger is the reactor.

For example, the output for the quenched product solution (QPS) has a flow rate out of the reactor, $F_{out}$, of 80 to about 1,000,000 mL/minute.

For example, the output for the quenched product solution (QPS) has a flow rate out of the reactor, $F_{out}$, of 100 to about 500,000 mL/minute.

For example, the output for the quenched product solution (QPS) has a flow rate out of the reactor, $F_{out}$, of 500 to about 100,000 mL/minute.

For example, the output for the quenched product solution (QPS) has a flow rate out of the reactor, $F_{out}$, of about 1,000 to about 10,000 mL/minute.

For example, the overall pressure in the reactor is 1 psi to 2000 psi.

For example, the overall pressure in the reactor is 1 psi to 1000 psi.

For example, the overall pressure in the reactor is 1 psi to 500 psi.

For example, the overall pressure in the reactor is 1 psi to 200 psi.

For example, the overall pressure in the reactor is 1 psi to 100 psi.

For example, the overall pressure in the reactor is 1 psi to 50 psi.

For example, the circulatory pump is an electrically powered centrifugal pump.

For example, the reactor further comprises one or more static mixers.

For example, the reactor is made of marine grade stainless steel piping.

For example, the reactor is made of nickel-alloy piping.

For example, the piping has Schedule 40 dimensions.

For example, the piping has Schedule 80 dimensions.

For example, the piping has Schedule 160 dimensions.

For example, the peroxide quenching solution (PQS) quenches the peroxide mixture (PM) oxidatively.

For example, the peroxide quenching solution (PQS) comprises nitric acid.

For example, the peroxide quenching solution (PQS) quenches the peroxide mixture (PM) reductively.

For example, the peroxide quenching solution (PQS) comprises thiodiglycol.

For example, the $C_4$-$C_{50}$ unsaturated material is a terpene, fatty acid ester, fatty acid, or vegetable oil.

For example, the peroxide mixture (PM) and a peroxide quenching solution (PQS) are recirculated through the reactor at least once before collecting the quenched product solution (QPS) from the output.

Provided herein is a method of continuously quenching a peroxide mixture (PM) in a single pass flow-through reactor as described herein.

For example, the peroxide mixture (PM) is derived from any $C_4$-$C_{50}$ unsaturated material.

For example, the peroxide mixture (PM) is derived from a terpene, fatty acid ester, fatty acid, or vegetable oil.

Provided herein is a method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) and a peroxide quenching solution (PQS) into a peroxide mixture (PM) and peroxide quenching solution (PQS) feeding chamber;

(e) feeding the peroxide mixture (PM) and peroxide quenching solution (PQS) into a single pass flow-through reactor as described herein.

Provided herein is a process for the preparation of compound of formula III,

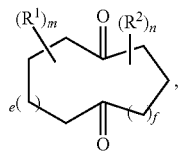

III comprising the quenching reaction of an ozonide of formula II,

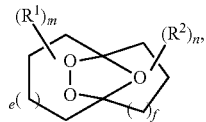

II wherein
R$^1$ and R$^2$ are independently selected from C$_1$-C$_{10}$ alkyl, C$_1$-C$_{10}$ hydroxyalkyl, C$_1$-C$_{10}$ haloalkyl and C$_1$-C$_{10}$ alkoxy; each of e, f, m, and n are independently are independently 0, 1, 2, 3, 4, 5, or 6; and wherein the quenching reaction is performed in the presence of one or more acids at a temperature of 40° C. to 140° C., wherein the quenching reaction optionally comprises quenching agent.

For example, the ozonide of formula II is prepared from the ozonolysis of a compound of formula I,

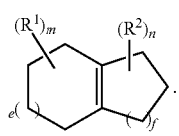

I

For example, R$^1$ and R$^2$ are independently selected from C$_1$-C$_6$ alkyl; and each of e, f, m, and n are independently 0, 1, or 2.

For example, m and n are independently selected from 0 and 1; and e and f are independently selected from 0, 1 and 2.

For example, the acid is acetic acid, propanoic acid, oxalic acid, hydrochloric acid, or sulfuric acid.

For example, the quenching reaction is performed at temperature of 60° C. to 110° C.

For example, the quenching reaction is performed at temperature of 80° C. to 110° C.

For example, the quenching reaction comprises a quenching reagent selected from bisulfite, triphenyl phosphine, dimethyl sulfide, thiodiglycol, and catalytic hydrogenation.

For example, the quenching reaction comprises a quenching reagent, wherein the quenching reagent is thiodiglycol.

For example, the molar ratio of the quenching reagent to the ozonide of formula II is 0.25 to 1, 0.5 to 1.0, 0.75 to 1, 1 to 1, 1.25 to 1, 1.5 to 1, 1.75 to 1, 2.0 to 1, 2.25 to 1, 2.5 to 1, 2.75 to 1, or 3.0 to 1.

For example, the molar ratio of the quenching reagent to the ozonide of formula II is 0.5 to 1.0, 0.75 to 1, 1 to 1, or 1.25 to 1.

Provided herein is a process for the preparation of compound IIIa,

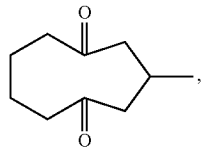

IIIa comprising the quenching reaction of ozonide IIa,

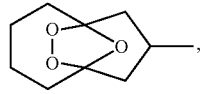

wherein the quenching reaction is performed in the presence of one or more acids at a temperature of 80° C. to 140° C., wherein the quenching reaction optionally comprises quenching agent.

For example, ozonide IIa is prepared from the ozonolysis of compound Ia,

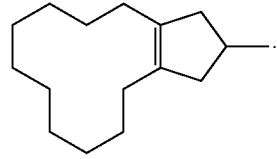 [SMILES: CC1CC2=C(CCCCCCCCCC2)C1]

For example, the acid is acetic acid, propanoic acid, oxalic acid, hydrochloric acid, or sulfuric acid.

For example, the quenching reaction comprises a quenching reagent selected from bisulfite, triphenyl phosphine, dimethyl sulfide, thiodiglycol, and catalytic hydrogenation.

For example, the quenching reaction comprises a quenching reagent, wherein the quenching reagent is thiodiglycol.

For example, the molar ratio of the quenching reagent to the ozonide of formula II is 0.25 to 1, 0.5 to 1.0, 0.75 to 1, 1 to 1, 1.25 to 1, 1.5 to 1, 1.75 to 1, 2.0 to 1, 2.25 to 1, 2.5 to 1, 2.75 to 1, or 3.0 to 1.

For example, the molar ratio of the quenching reagent to the ozonide of formula II is 0.5 to 1.0, 0.75 to 1, 1 to 1, or 1.25 to 1.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE FIGURES

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

The application pertains to flow-through reactors for the continuous quenching of a peroxide mixture (PM). In one aspect, the flow-through reactors are single-pass flow-through reactors. In one aspect, the flow-through reactors are recirculating flow-through reactors. Unless explicitly indicated otherwise, all of the embodiments disclosed in the application may apply to either type of flow-through reactor.

Figure 1:
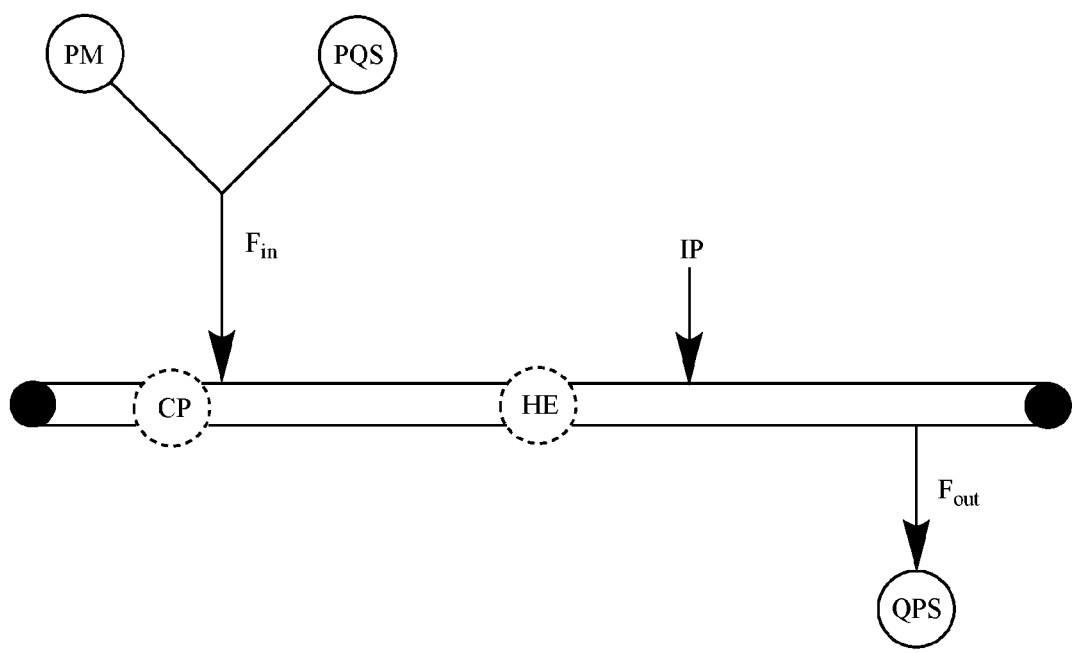
FIG. 1. Basic Diagram of a single-pass flow-through reactor for the continuous quenching of a peroxide mixture (PM) via single input of the peroxide mixture (PM) and a peroxide quenching solution (PQS) into the reactor.

This application pertains to a single-pass flow-through reactor for the continuous quenching of a peroxide mixture (PM), as illustrated in FIG. 1, said reactor comprising:

a single input for both a peroxide mixture (PM) and a peroxide quenching solution (PQS);

an output for a quenched product solution (QPS); and optionally, a circulatory pump (CP), a heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

Figure 3:
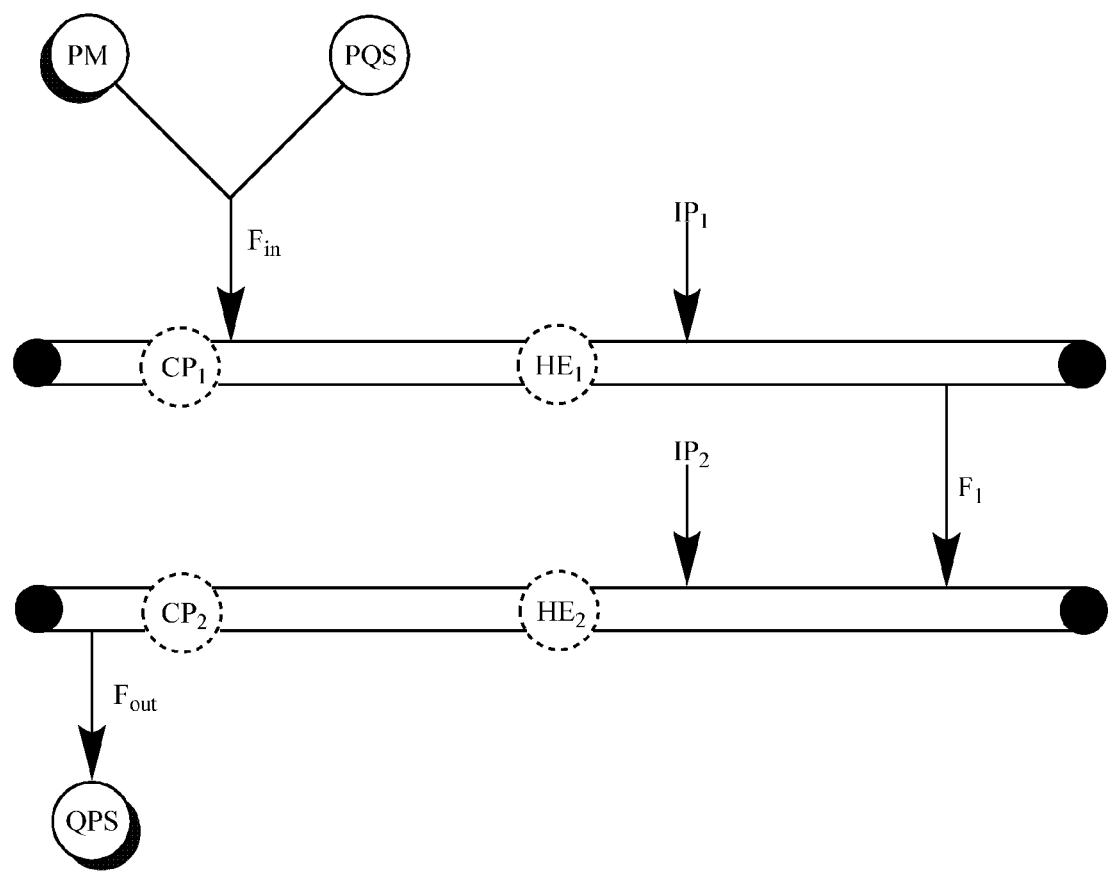
FIG. 3. Basic Diagram of two single-pass flow-through reactors connected in series for the continuous quenching of a peroxide mixture (PM) via single input of the peroxide mixture (PM) and a peroxide quenching solution (PQS) into the first single pass reactor.

This application pertains to a single-pass flow-through reactor for the continuous quenching of a peroxide mixture (PM), as illustrated in FIG. 3, said reactor comprising:

a single input for both a peroxide mixture (PM) and a peroxide quenching solution (PQS);

an output for a quenched product solution (QPS); and optionally, a circulatory pump (CP), a heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the reactor further comprises:

a second single-pass flow-through reactor connected to the first single-pass flow-through reactor, said second reactor optionally comprising a circulatory pump (CP), heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the flow in the reactor has a flow rate, F, the input for the peroxide mixture (PM) and peroxide quenching solution (PQS) has a flow rate into the first reactor, $F_{in}$, and the output for the quenched product solution (QPS) has a flow rate out of the second reactor, $F_{out}$.

Figure 5:
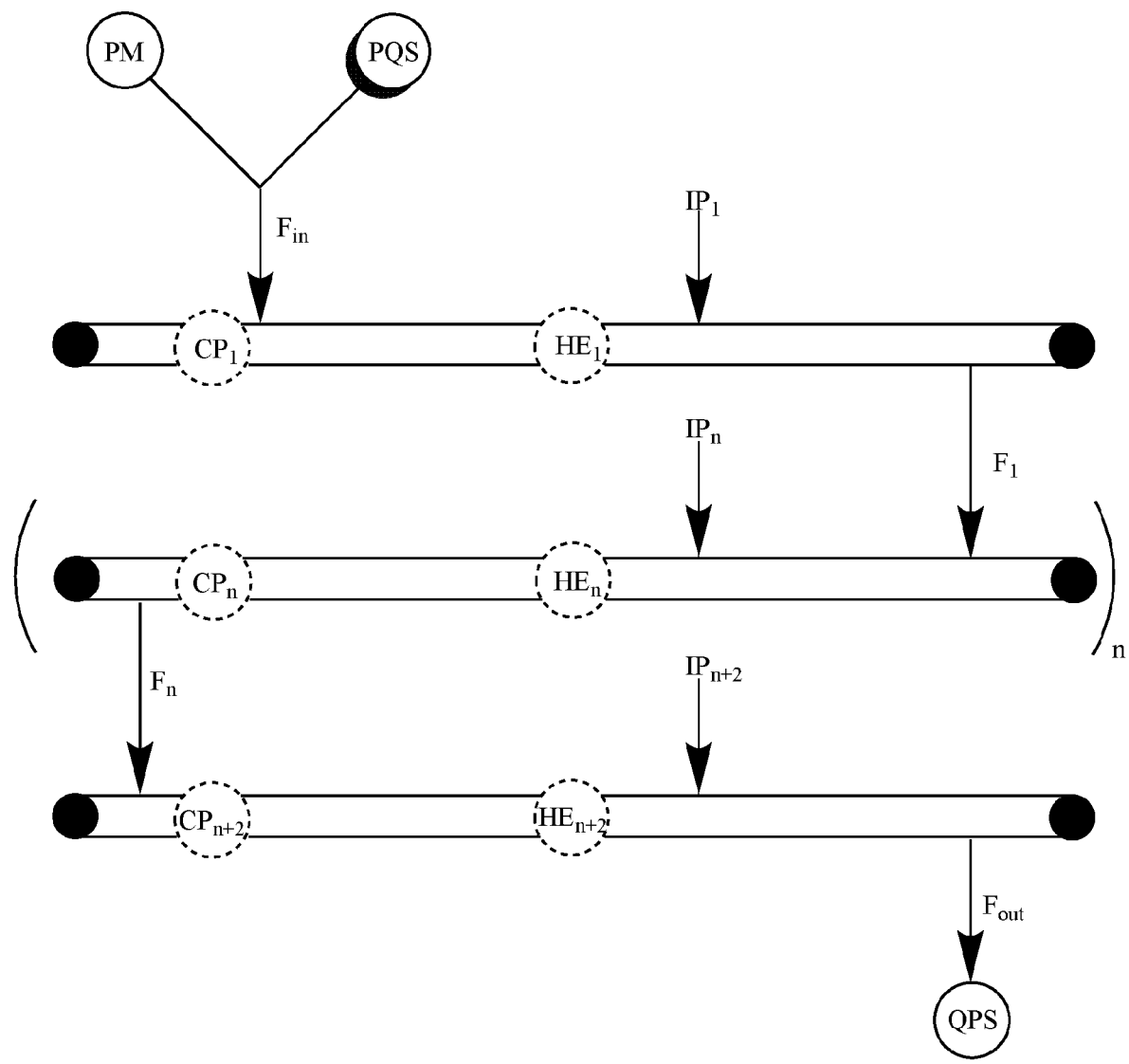
FIG. 5. Basic Diagram of multiple single-pass flow-through reactors connected in series for the continuous quenching of a peroxide mixture (PM) via single input of the peroxide mixture (PM) and a peroxide quenching solution (PQS) into the first single pass reactor.

This application pertains to a single-pass flow-through reactor for the continuous quenching of a peroxide mixture (PM), as illustrated in FIG. 5, said reactor comprising:

a single input for both a peroxide mixture (PM) and a peroxide quenching solution (PQS);

an output for a quenched product solution (QPS); and optionally, a circulatory pump (CP), a heat exchanger (HE), or both;

wherein the reactor further comprises:

n additional single-pass flow-through reactors connected in series to the first single-pass flow-through reactor, wherein each additional reactor optionally comprises a circulatory pump (CP), heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the flow in the reactor has a flow rate, F, the input for the peroxide mixture (PM) and peroxide quenching solution (PQS) has a flow rate into the first reactor, $F_{in}$, and the output for the quenched product solution (QPS) has a flow rate out of the last reactor, $F_{out}$;

wherein n is an integer greater than or equal to 2.

In one embodiment, n is an integer from 2 to 50.

In one embodiment, n is an integer from 2 to 100, 2 to 90, 2 to 80, 2 to 70, 2 to 60, 2 to 50, 2 to 40, 2 to 30, 2 to 30, or 2 to 20.

In one embodiment, n is selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100.

Figure 2:
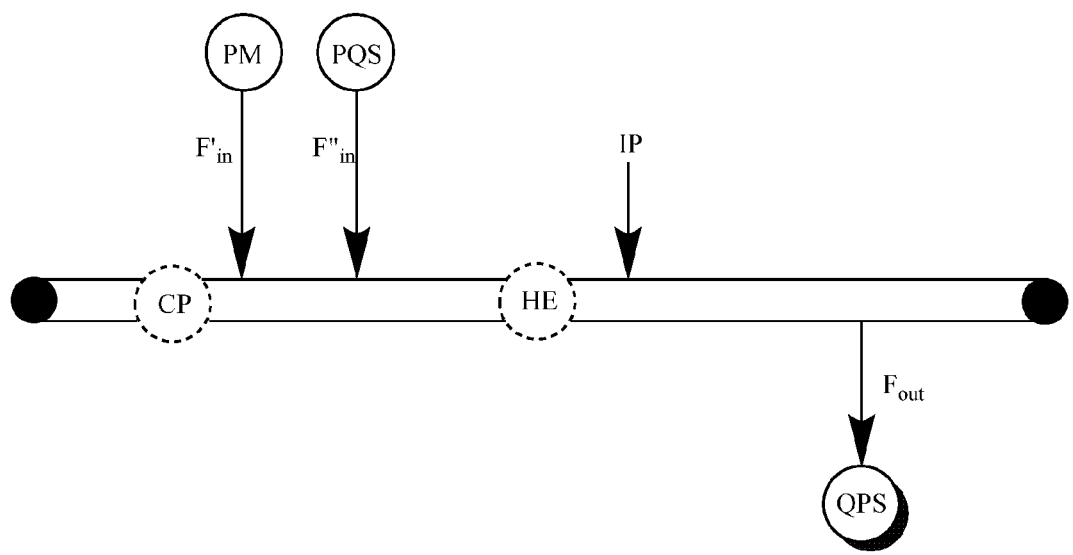
FIG. 2. Basic Diagram of a single-pass flow-through reactor for the continuous quenching of a peroxide mixture (PM) via separate inputs of the peroxide mixture (PM) and a peroxide quenching solution (PQS) into the reactor.

This application pertains to a single-pass flow-through reactor for the continuous quenching of a peroxide mixture (PM), as illustrated in FIG. 2, said reactor comprising:

a first input for a peroxide mixture (PM);
a second input for a peroxide quenching solution (PQS);

an output for a quenched product solution (QPS); and, optionally, a circulatory pump (CP), a heat exchanger (HE), or both;

wherein the flow in the reactor has a flow rate, F, the first input for the peroxide mixture (PM) has a flow rate into the reactor, $F'_{in}$, the second input for the peroxide quenching solution (PQS) has a flow rate into the reactor, $F''_{in}$, and the output for the quenched product solution (QPS) has a flow rate out of the reactor, $F_{out}$.

Figure 4:
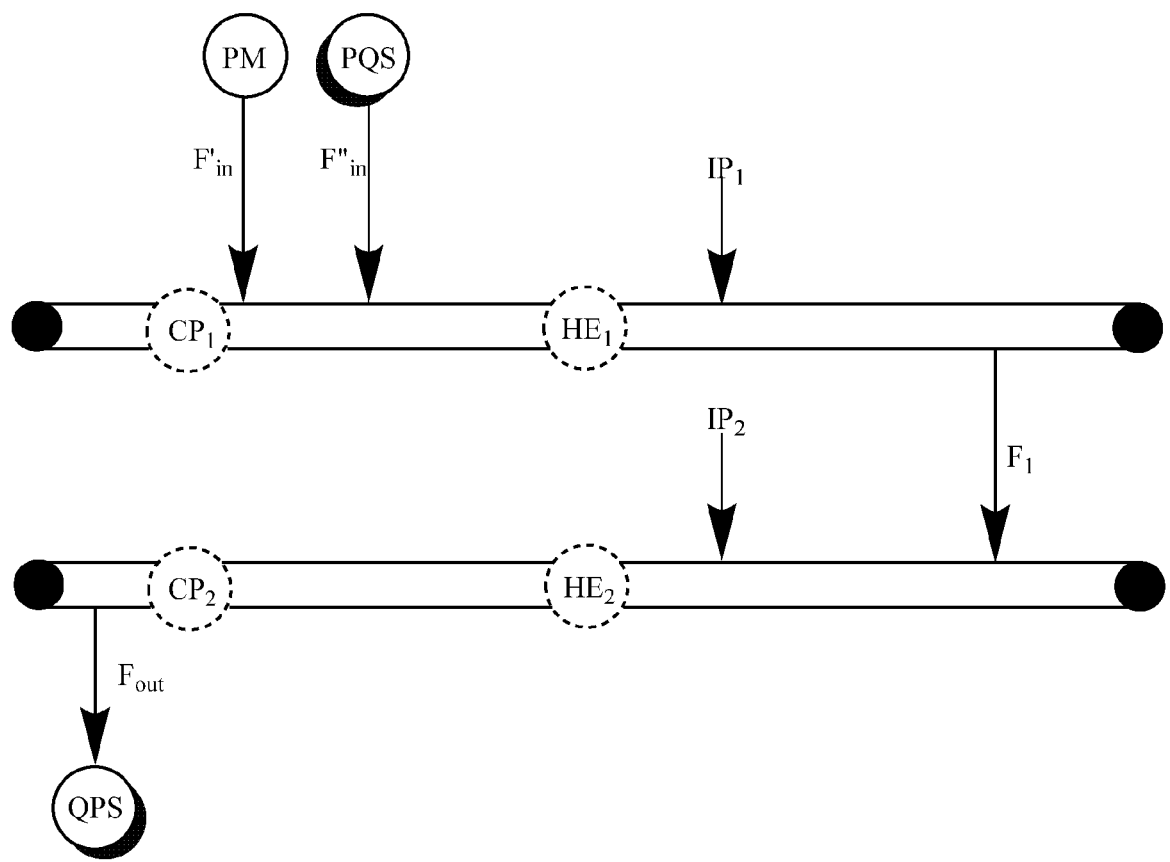
FIG. 4. Basic Diagram of two single-pass flow-through reactors connected in series for the continuous quenching of a peroxide mixture (PM) via separate inputs of the peroxide mixture (PM) and a peroxide quenching solution (PQS) into the first single pass reactor.

This application pertains to a single-pass flow-through reactor for the continuous quenching of a peroxide mixture (PM), as illustrated in FIG. 4, said reactor comprising:

a first input for a peroxide mixture (PM);
a second input for a peroxide quenching solution (PQS);
an output for a quenched product solution (QPS); and, optionally, a circulatory pump (CP), a heat exchanger (HE), or both;

wherein the reactor further comprises:

a second single-pass flow-through reactor connected to the first single-pass flow-through reactor, said second reactor optionally comprising a circulatory pump (CP), heat exchanger (HE), or both;

wherein the flow in the reactor has a flow rate, F, the first input for the peroxide mixture (PM) has a flow rate into the first reactor, $F'_{in}$, the second input for the peroxide quenching solution (PQS) has a flow rate into the first reactor, $F''_{in}$, and the output for the quenched product solution (QPS) has a flow rate out of the second reactor, $F_{out}$.

Figure 6:
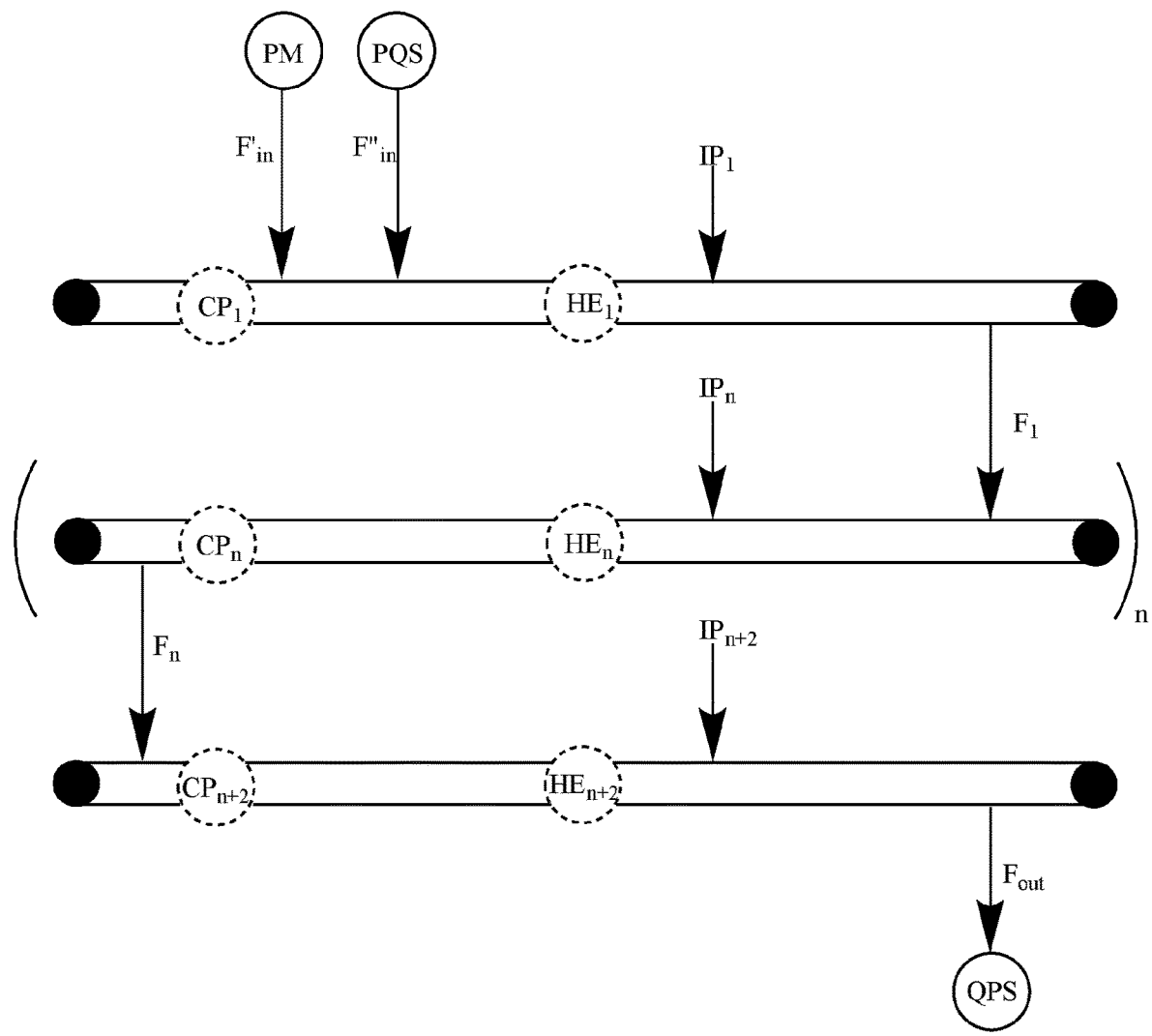
FIG. 6. Basic Diagram of multiple single-pass flow-through reactors connected in series for the continuous quenching of a peroxide mixture (PM) via separate inputs of the peroxide mixture (PM) and a peroxide quenching solution (PQS) into the first single pass reactor.

This application pertains to a single-pass flow-through reactor for the continuous quenching of a peroxide mixture (PM), as illustrated in FIG. 6, said reactor comprising:

a first input for a peroxide mixture (PM);
a second input for a peroxide quenching solution (PQS);
an output for a quenched product solution (QPS); and, optionally, a circulatory pump (CP), a heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the reactor further comprises:

n additional single-pass flow-through reactors connected in series to the first single-pass flow-through reactor, wherein each additional reactor optionally comprises a circulatory pump (CP), heat exchanger (HE), or both;

wherein the flow in the reactor has a flow rate, F, the first input for the peroxide mixture (PM) has a flow rate into the first reactor, $F'_{in}$, the second input for the peroxide quenching solution (PQS) has a flow rate into the first reactor, $F''_{in}$, and the output for the quenched product solution (QPS) has a flow rate out of the last reactor, $F_{out}$;

wherein n is an integer greater than or equal to 2.

In one embodiment, n is an integer from 2 to 50.

In one embodiment, n is an integer from 2 to 100, 2 to 90, 2 to 80, 2 to 70, 2 to 60, 2 to 50, 2 to 40, 2 to 30, 2 to 30, or 2 to 20.

In one embodiment, n is selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100.

Figure 7:
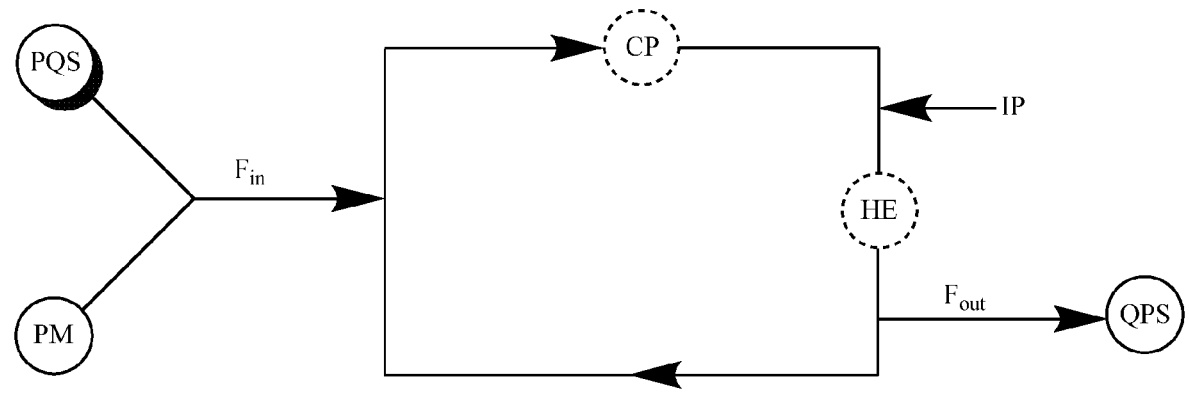
FIG. 7. Basic Diagram of a recirculating flow-through reactor for the continuous quenching of a peroxide mixture (PM) via single input of the peroxide mixture (PM) and a peroxide quenching solution (PQS) into the reactor.

This application pertains to a recirculating flow-through reactor, as illustrated in FIG. 7, for the continuous quenching of a peroxide mixture (PM), said reactor comprising:

a single input for both a peroxide mixture (PM) and a peroxide quenching solution (PQS);

an output for a quenched product solution (QPS); and, optionally, a circulatory pump (CP), a heat exchanger (HE), or both, i.e., a means for heating or for heat removal (HE);

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

For example, the flow rate of the peroxide mixture (PM) and peroxide quenching solution (PQS) into the reactor is $F_{in}$, which is about equal to the flow rate of the quenched product solution (QPS) out of the reactor, $F_{out}$.

For example, the flow rate of the peroxide mixture (PM) and peroxide quenching solution (PQS) into the reactor is $F_{in}$, which is equal to the flow rate of the quenched product solution (QPS) out of the reactor, $F_{out}$.

For example, the reactor also contains an injection port (IP), which is primarily for obtaining a sample of the material in the reactor for analysis. In one example, the analysis is an iodometric titration to determine the peroxide concentration in the reactor.

Figure 8:
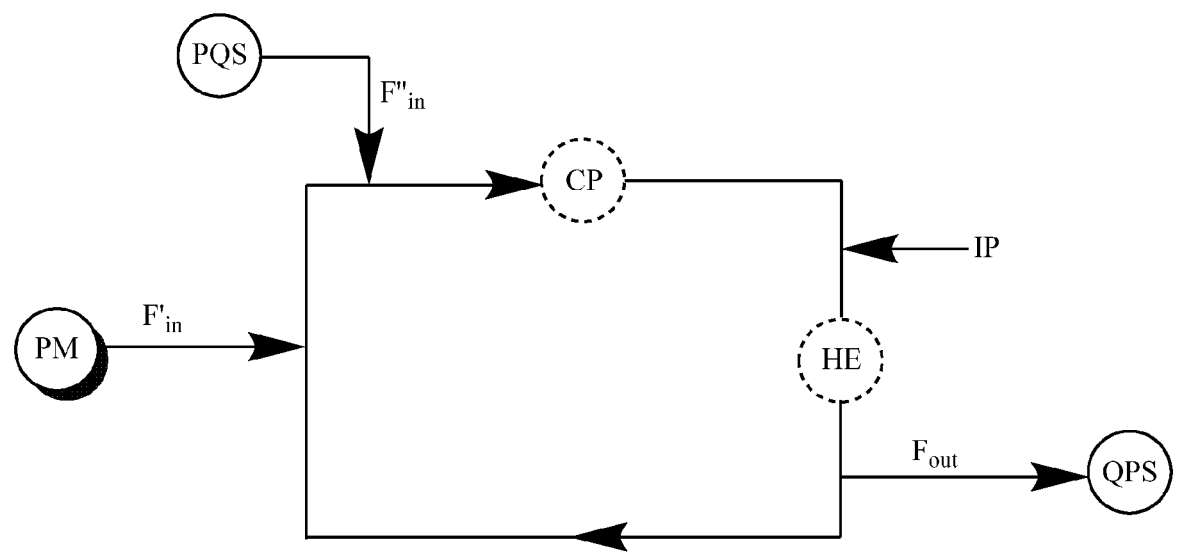
FIG. 8. Basic Diagram of a recirculating flow-through reactor for the continuous quenching of a peroxide mixture (PM) via separate inputs of the peroxide mixture (PM) and a peroxide quenching solution (PQS) into the reactor.

This application pertains to a recirculating flow-through reactor, as illustrated in FIG. 8, for the continuous quenching of a peroxide mixture (PM), said reactor comprising:

a first input for a peroxide mixture (PM);

a second input for a peroxide quenching solution (PQS);

an output for a quenched product solution (QPS); and, optionally, a circulatory pump (CP), a heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both; wherein the flow in the reactor has a flow rate, F, the first input for the peroxide mixture (PM) has a flow rate into the reactor, $F'_{in}$, the second input for the peroxide quenching solution (PQS) has a flow rate into the reactor, $F''_{in}$, and the output for the quenched product solution (QPS) has a flow rate out of the reactor, $F_{out}$.

For example, the sum of the flow rate of the peroxide mixture (PM) into the reactor, $F'_{in}$, and the flow rate of peroxide quenching solution (PQS) into the reactor, $F''_{in}$, is about equal to the flow rate of the quenched product solution (QPS) out of the reactor, $F_{out}$.

For example, the sum of the flow rate of the peroxide mixture (PM) into the reactor, $F_{in}$, and the flow rate of peroxide quenching solution (PQS) into the reactor, $F''_{in}$, is equal to the flow rate of the quenched product solution (QPS) out of the reactor, $F_{out}$.

For example, the flow rate in the reactor, F, is greater than the flow rate of the quenched product solution (QPS) out of the reactor, $F_{out}$.

Figure 9:
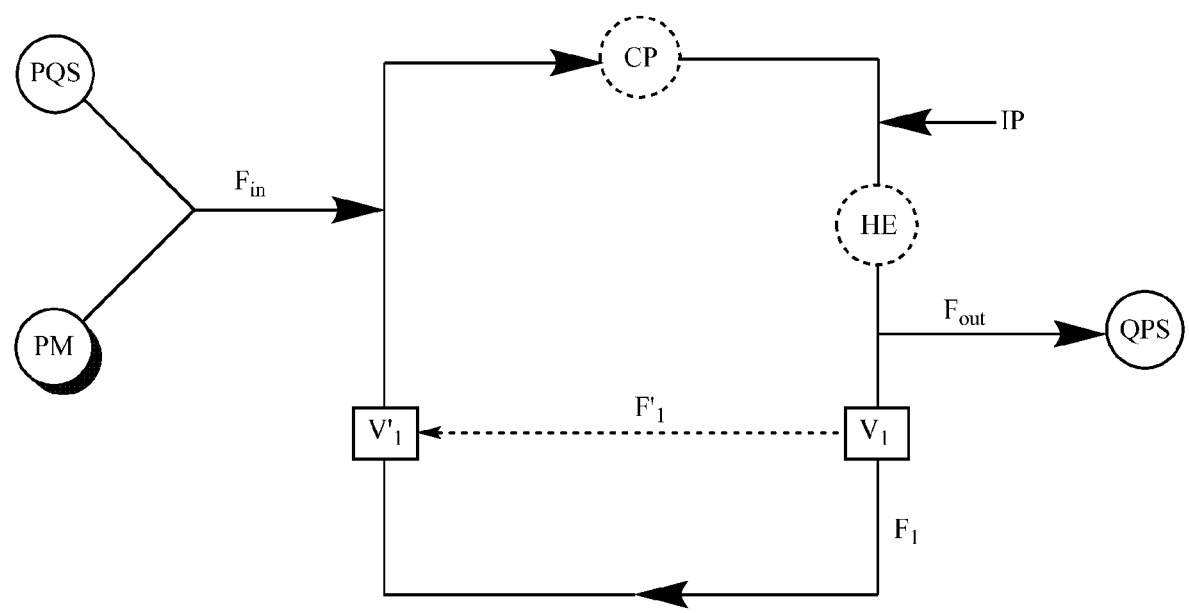
FIG. 9. Basic Diagram of a recirculating flow-through reactor for the continuous quenching of a peroxide mixture (PM) via single input of the peroxide mixture (PM) and a peroxide quenching solution (PQS) into the reactor, further comprising additional piping attached to the reactor through valves set to permit flow into the additional piping.
Figure 10:
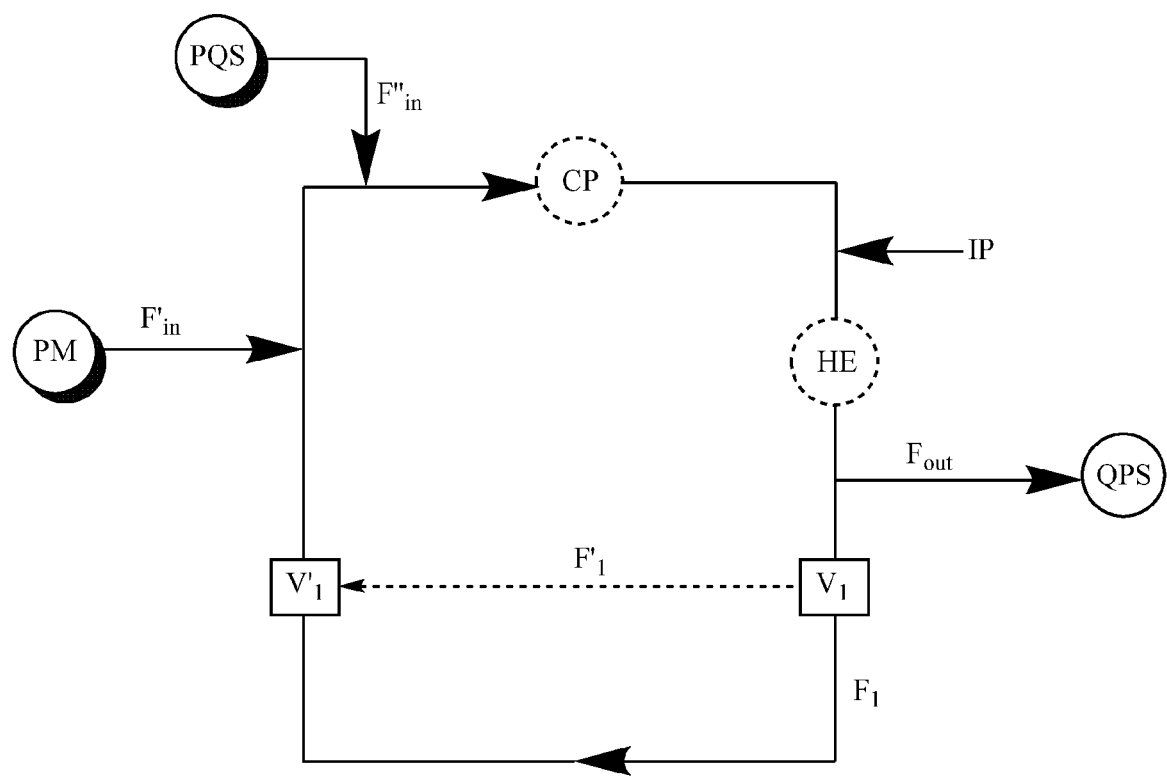
FIG. 10. Basic Diagram of a recirculating flow-through reactor for the continuous quenching of a peroxide mixture (PM) via separate inputs of the peroxide mixture (PM) and a peroxide quenching solution (PQS) into the reactor, further comprising additional piping attached to the reactor through valves set to permit flow into the additional piping.

This application pertains to a recirculating flow-through reactor, as illustrated in FIGS. 9 and 10, wherein any of the recirculating flow-through reactors described herein further comprise additional piping attached to the reactor through valves $V_1$ and $V'_1$, wherein $V_1$ is set to permit flow into the additional piping ($F_1$) and $V'_1$ is set to restrict flow back to $V_1$.

Figure 11:
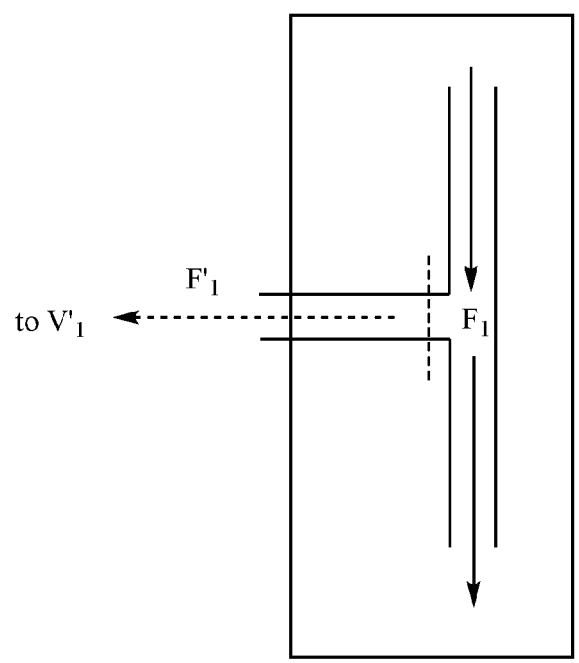
FIG. 11. Structure and Flow Diagram of valve $V_1$.

For example, Valve $V_1$, as illustrated in FIG. 11, is set to allow flow into the additional piping, $F_1$ and to restrict flow to Valve $V'_1$, i.e., $F_1 \gg F'_1$. In one example, flow to Valve $V'_1$ is completely restricted. In one example, flow to Valve $V'_1$ is nearly completely restricted.

For example Valve $V'_1$, is set to restrict flow back to Valve $V_1$. In one example, flow back to Valve $V_1$ is completely restricted. In one example, flow back to Valve $V_1$ is nearly completely restricted.

Figure 12:
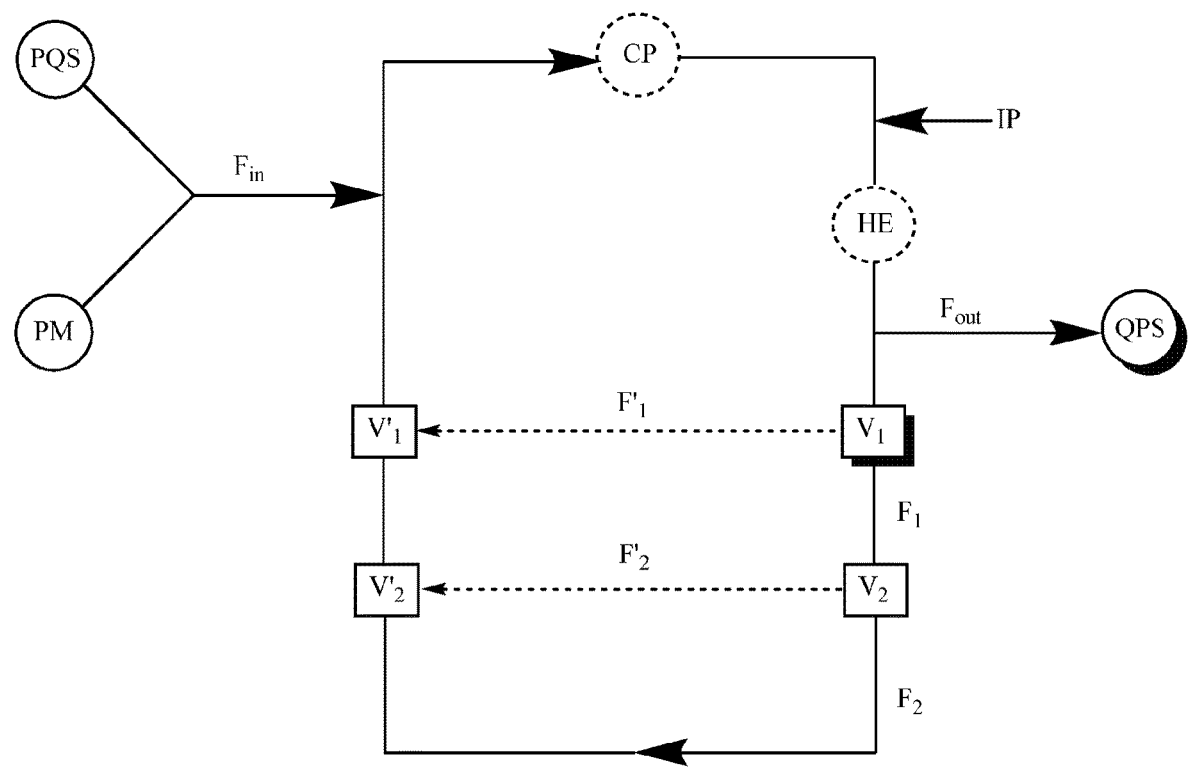
FIG. 12. Basic Diagram of a recirculating flow-through reactor for the continuous quenching of a peroxide mixture (PM) via single input of the peroxide mixture (PM) and a peroxide quenching solution (PQS) into the reactor, further comprising additional piping attached to the reactor through two series of valves set to permit flow into the additional piping.
Figure 13:
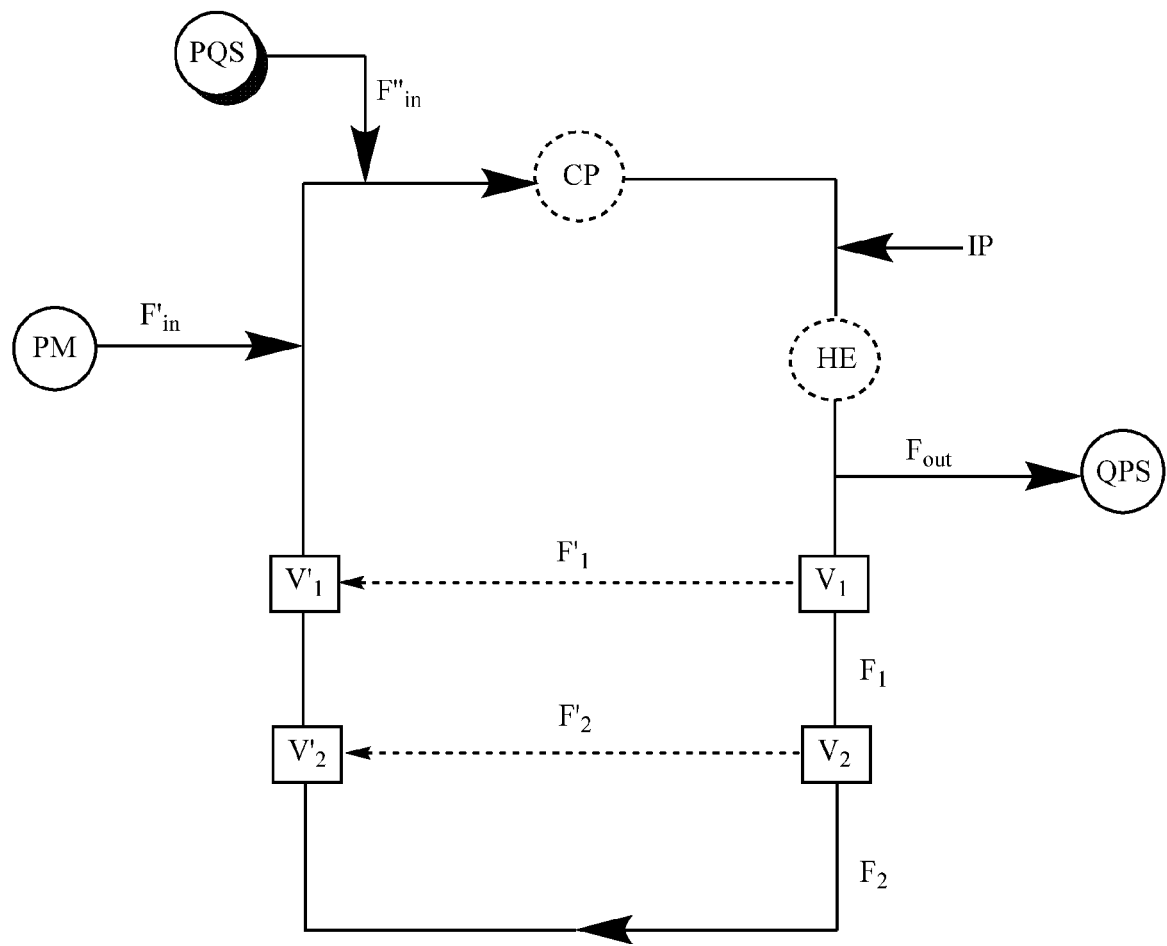
FIG. 13. Basic Diagram of a recirculating flow-through reactor for the continuous quenching of a peroxide mixture (PM) via separate inputs of the peroxide mixture (PM) and a peroxide quenching solution (PQS) into the reactor, further comprising additional piping attached to the reactor through two series of valves set to permit flow into the additional piping.

This application pertains to a recirculating flow-through reactor, as illustrated in FIGS. 12 and 13, wherein the recirculating flow-through reactor described above further comprises additional piping attached to said reactor through valves $V_2$ and $V'_2$, wherein $V_2$ is set to permit flow into the additional piping ($F_2$) and $V'_2$ is set to restrict flow back to $V_2$.

For example, Valve $V_2$ is set to allow flow into the additional piping, $F_2$, and to restrict flow to Valve $V'_2$, i.e., $F_2 \gg F'_2$. In one example, flow to Valve $V'_2$ is completely restricted. In one example, flow to Valve $V'_2$ is nearly completely restricted.

For example Valve $V'_2$, is set to restrict flow back to Valve $V_2$. In one example, flow back to Valve $V_2$ is completely restricted. In one example, flow back to Valve $V_2$ is nearly completely restricted.

Figure 14:
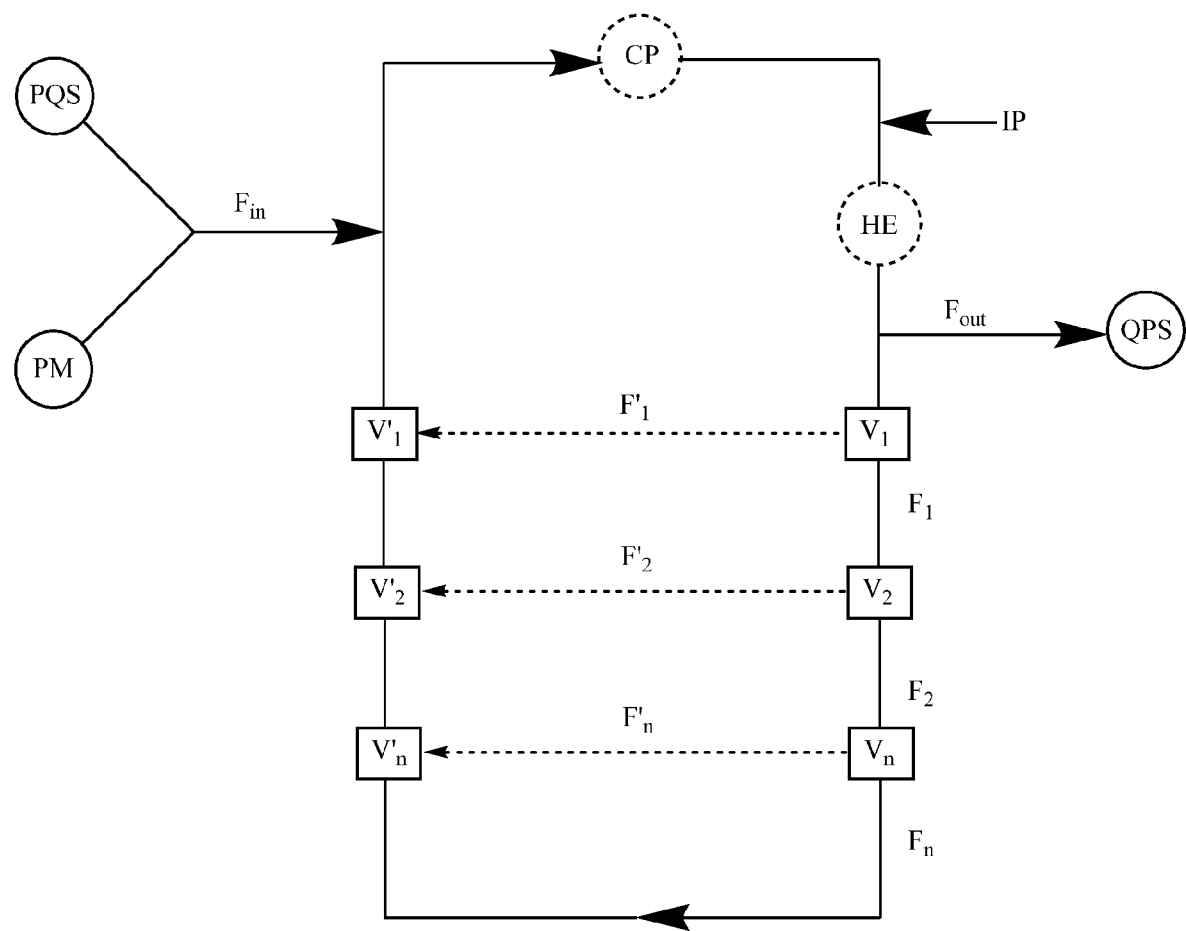
FIG. 14. Basic Diagram of a recirculating flow-through reactor for the continuous quenching of a peroxide mixture (PM) via single input of the peroxide mixture (PM) and a peroxide quenching solution (PQS) into the reactor, further comprising additional piping attached to the reactor through multiple (three or more) series of valves set to permit flow into the additional piping.
Figure 15:
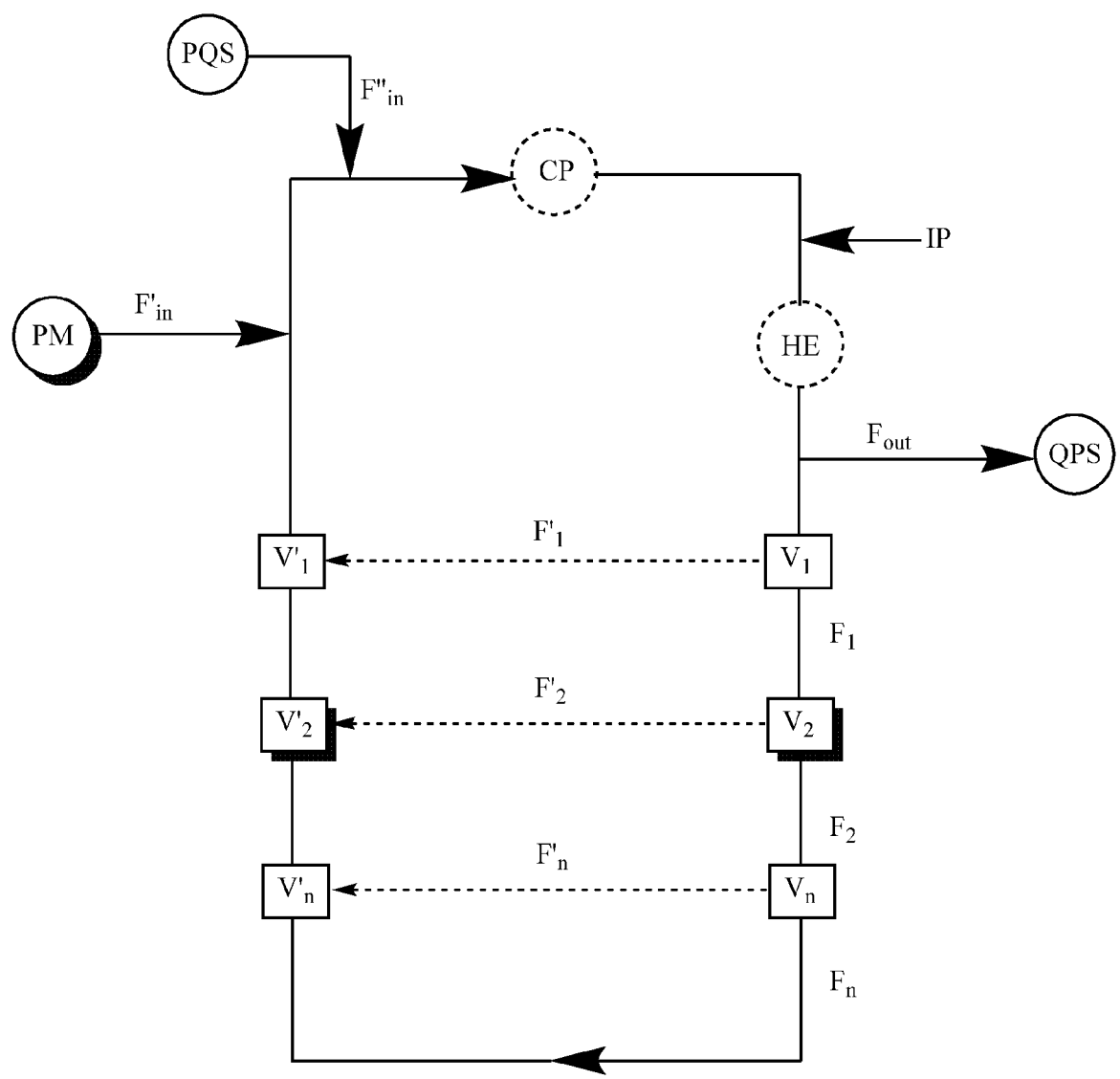
FIG. 15. Basic Diagram of a recirculating flow-through reactor for the continuous quenching of a peroxide mixture (PM) via separate inputs of the peroxide mixture (PM) and a peroxide quenching solution (PQS) into the reactor, further comprising additional piping attached to the reactor through multiple (three or more) series of valves set to permit flow into the additional piping.
Figure 16:
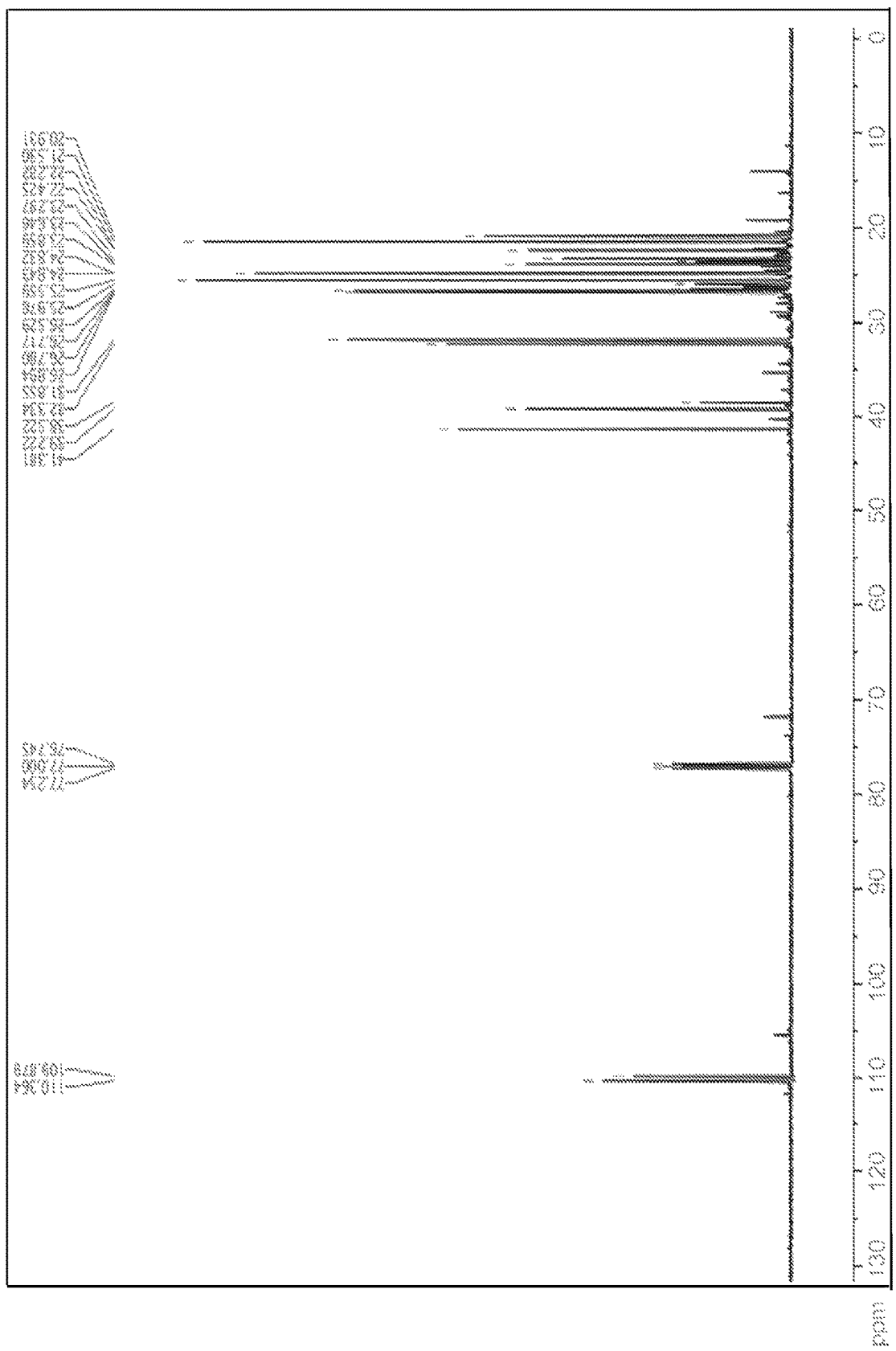
FIG. 16. $^{13}C$ NMR spectrum of the isolated, stable ozonide compound IIa, which is a mixture of two conformers.

This application pertains to a recirculating flow-through reactor, as illustrated in FIGS. 14 and 15, wherein any of the recirculating flow-through reactors described herein further additional piping attached to the reactor through multiple sets of valves $V_n$ and $V'_n$, wherein $V_n$ is set to permit flow into the additional piping ($F_n$) and $V'_n$ is set to restrict flow back to $V_n$.

For example, Valve $V_n$, may be set to allow flow into the additional piping, $F_1$, and to restrict flow to Valve $V'_n$, i.e., $F_1 \gg F'_1$. In one example, flow to Valve $V'_n$ is completely restricted. In one example, flow to Valve $V'_n$ is nearly completely restricted.

For example Valve $V'_n$, is set to restrict flow back to Valve $V_n$. In one example, flow back to Valve $V_n$ is completely restricted. In one example, flow back to Valve $V_n$ is nearly completely restricted.

For example, n is an integer from 3 to 100. For example, n is an integer from 3 to 20. For example, n is an integer from 3 to 10.

This application pertains to any of the reactors described herein, wherein the reactor is placed in line, i.e., connected to, with an ozonolysis operation.

This application pertains to any of the reactors described herein, wherein the reactor is placed in line with a continuous ozonolysis operation from a tubular falling film reactor system with one or multiple tubes wherein the combined ozone and carrier gas flow is co-current.

This application pertains to any of the recirculating flow-through reactors disclosed herein, where the peroxide mixture (PM) and the peroxide quenching solution (PQS) are recirculated through the reactor several times before collecting the quenched product solution (QPS) from the output.

In one embodiment, the peroxide mixture (PM) and the peroxide quenching solution (PQS) are recirculated through the recirculating flow-through reactor at least 100 times, at least 90 times, at least 80 times, at least 70 times, at least 60 times, at least 50 times, at least 40 times, at least 30 times, at least 20 times, at least 10 time, or at least 5 times before collecting the quenched product solution (QPS) from the output.

In one embodiment, the peroxide mixture (PM) and the peroxide quenching solution (PQS) are recirculated through the recirculating flow-through reactor 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 times before collecting the quenched product solution (QPS) from the output.

In one embodiment, the peroxide mixture (PM) and the peroxide quenching solution (PQS) are recirculated through the recirculating flow-through reactor as many times as necessary before collecting the quenched product solution (QPS) from the output. The necessary number of recirculations needed to achieve an acceptable conversion of the peroxide mixture (PM) may be determined by iodometric titration.

This application pertains to a method of continuously quenching a peroxide mixture (PM) using any of the single pass flow-through reactors disclosed in the application.

This application pertains to a method of continuously quenching a peroxide mixture (PM) using any of the single pass flow-through reactors disclosed in the application, wherein the wherein the peroxide mixture (PM) is derived from any $C_4$-$C_{50}$ unsaturated material. For example, the peroxide mixture (PM) is derived from a terpene, fatty acid ester, fatty acid, or vegetable oil.

This application pertains to a method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) and a peroxide quenching solution (PQS) into a peroxide mixture (PM) and peroxide quenching solution (PQS) feeding chamber;

(e) feeding the peroxide mixture (PM) and peroxide quenching solution (PQS) into a single pass flow-through reactor disclosed in the application.

This application pertains to a method of continuously quenching a peroxide mixture (PM) in a recirculating flow-through reactor, said reactor comprising:

a single input for both a peroxide mixture (PM) and a peroxide quenching solution (PQS);

an output for a quenched product solution (QPS); and, optionally, a circulatory pump (CP), a heat exchanger (HE), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

This application pertains to a method of continuously quenching a peroxide mixture (PM) in a recirculating flow-through reactor, said reactor comprising:

a first input for a peroxide mixture (PM);

a second input for a peroxide quenching solution (PQS);

an output for a quenched product solution (QPS); and, optionally, a circulatory pump (CP), a heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the flow in the reactor has a flow rate, F, the first input for the peroxide mixture (PM) has a flow rate into the reactor, $F'_{in}$, the second input for the peroxide quenching solution (PQS) has a flow rate into the reactor, $F''_{in}$, and the output for the quenched product solution (QPS) has a flow rate out of the reactor, $F_{out}$.

This application pertains to a method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent recirculating flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) and a peroxide quenching solution (PQS) into a peroxide mixture (PM) and peroxide quenching solution (PQS) feeding chamber;

(e) feeding the peroxide mixture (PM) and peroxide quenching solution (PQS) into a recirculating flow-through reactor for the continuous quenching of the peroxide mixture (PM), said reactor comprising:

(i) a single input for both a peroxide mixture (PM) and a peroxide quenching solution (PQS);

(ii) an output for a quenched product solution (QPS); and, (iii) optionally, a circulatory pump (CP), a heat exchanger (HE) (e.g., the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger), or both;

wherein the flow in the reactor has a flow rate, F, the input for the peroxide mixture (PM) and peroxide quenching solution (PQS) has a flow rate into the reactor, $F_{in}$, and the output for the quenched product solution (QPS) has a flow rate out of the reactor, $F_{out}$.

This application pertains to a method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

(a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) into a recirculating flow-through reactor for the continuous quenching of the peroxide mixture (PM), said reactor comprising:
(i) a first input for a peroxide mixture (PM);
(ii) a second input for a peroxide quenching solution (PQS);
(iii) an output for a quenched product solution (QPS); and,
(iv) optionally, a circulatory pump (CP), a heat exchanger (HE), or both;

wherein the flow in the reactor has a flow rate, F, the first input for the peroxide mixture (PM) has a flow rate into the reactor, $F_{in}$, the second input for the peroxide quenching solution (PQS) has a flow rate into the reactor, $F''_{in}$, and the output for the quenched product solution (QPS) has a flow rate out of the reactor, $F_{out}$.

This application pertains to any of the methods of continuously quenching a peroxide mixture (PM) in a recirculating flow-through reactor disclosed herein, where the peroxide mixture (PM) and the peroxide quenching solution (PQS) are recirculated through the reactor several times before collecting the quenched product solution (QPS) from the output.

In one embodiment, the peroxide mixture (PM) and the peroxide quenching solution (PQS) are recirculated through the recirculating flow-through reactor at least 100 times, at least 90 times, at least 80 times, at least 70 times, at least 60 times, at least 50 times, at least 40 times, at least 30 times, at least 20 times, at least 10 time, or at least 5 times before collecting the quenched product solution (QPS) from the output.

In one embodiment, the peroxide mixture (PM) and peroxide quenching solution (PQS) are recirculated through the recirculating flow-through reactor 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 times before collecting the quenched product solution (QPS) from the output.

In one embodiment, any of the flow-through reactors of the application is configured to have one or more heating elements so that the temperature inside the reactor can be warmed or cooled as desired at different points along the reactor. For example, the reactor can comprise two, three, four, five, six, or more heating elements so that the temperature inside the reactor can be warmed or cooled as desired at different points along the reactor.

In one embodiment, several, i.e., 3 to 100, single-pass flow-through reactors may be connected in series and each reactor may or may not have a heating element such as shell-in-tube heating elements or gasketed plate-and-frame type heating elements. In one embodiment, the heating element could comprise the vast majority of volume or the entire volume of any single-pass flow-through reactor. In one embodiment, the heating element could comprise the vast majority of volume or the entire volume of a few, most, or all of the single-pass flow-through reactors connected in series.

In another embodiment, any of the flow-through reactors of the application could be largely composed of heating and cooling elements. For example, heat exchanger elements of the shell-in-tube or gasketed plate-and-frame type could comprise the vast majority of the volume or all of the volume of the reactor.

For example, for any of the reactors of the application or methods comprising the reactors of the application, the heat exchanger (HE) maintains the temperature in the reactor at −78° C. to 300° C.

For example, for any of the reactors of the application or methods comprising the reactors of the application, the heat exchanger (HE) maintains the temperature in the reactor at −40° C. to 150° C.

For example, for any of the reactors of the application or methods comprising the reactors of the application, the heat exchanger (HE) maintains the temperature in the reactor at −25° C. to 29° C.

For example, for any of the reactors of the application or methods comprising the reactors of the application, the heat exchanger (HE) maintains the temperature in the reactor at 0° C. to 100° C.

For example, for any of the reactors of the application or methods comprising the reactors of the application, the heat exchanger (HE) maintains the temperature in the reactor at 0° C. to 29° C.

For example, for any of the reactors of the application or methods comprising the reactors of the application, the heat exchanger (HE) maintains the temperature in the reactor at 20° C. to 100° C.

For example, for any of the reactors of the application or methods comprising the reactors of the application, the heat exchanger (HE) maintains the temperature in the reactor at 20° C. to 80° C.

For example, for any of the reactors of the application or methods comprising the reactors of the application, the heat exchanger (HE) maintains the temperature in the reactor at 20° C. to 60° C.

For example, for any of the reactors of the application or methods comprising the reactors of the application, the heat exchanger (HE) maintains the temperature in the reactor at 60° C. to 110° C.

For example, for any of the reactors of the application or methods comprising the reactors of the application, the heat exchanger (HE) maintains the temperature in the reactor at 60° C. to 80° C.

For example, for any of the reactors of the application or methods comprising the reactors of the application, the heat exchanger (HE) maintains the temperature in the reactor at 80° C. to 110° C.

For example, for any of the reactors of the application or methods comprising the reactors of the application, the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger.

For example, for any of the reactors of the application or methods comprising the reactors of the application, the heat exchanger (HE) is an Alfa Laval brazed plate heat exchanger, an Alfa Laval fusion-bonded plate heat exchanger, an Alfa Laval gasketed plate-and-frame heat exchanger, an Alfa Laval welded plate-and-shell heat exchanger, an Alfa Laval welded plate-and-block heat exchanger, an Alfa Laval printed circuit heat exchanger, an Alfa Laval welded spiral heat exchanger, or an Alfa Laval welded plate-and-frame heat exchanger.

For example, for any of the reactors of the application or methods comprising the reactors of the application, the heat exchanger (HE) is an Alfa Laval gasketed plate-and-frame heat exchanger.

For example, for any of the reactors of the application or methods comprising the reactors of the application, the heat exchanger (HE) is the reactor, i.e., the heat exchanger and the reactor are one and the same.

For example, for any of the reactors of the application or methods comprising the reactors of the application, the overall peroxide concentration in the peroxide mixture (PM) prior to entering the reactor is 400-3000 mmol/L as determined by iodometric titration.

For example, for any of the reactors of the application or methods comprising the reactors of the application, the overall peroxide concentration in the peroxide mixture (PM) prior to entering the reactor is 500-2000 mmol/L as determined by iodometric titration.

For example, for any of the reactors of the application or methods comprising the reactors of the application, the overall peroxide concentration in the peroxide mixture (PM) prior to entering the reactor is 2500-3000 mmol/L as determined by iodometric titration.

For example, for any of the reactors of the application or methods comprising the reactors of the application, the overall peroxide concentration in the peroxide mixture (PM) prior to entering the reactor is 2000-2500 mmol/L as determined by iodometric titration.

For example, for any of the reactors of the application or methods comprising the reactors of the application, the overall peroxide concentration in the peroxide mixture (PM) prior to entering the reactor is 1500-2000 mmol/L as determined by iodometric titration.

For example, for any of the reactors of the application or methods comprising the reactors of the application, the overall peroxide concentration in the peroxide mixture (PM) prior to entering the reactor is 1000-1500 mmol/L as determined by iodometric titration.

For example, for any of the reactors of the application or methods comprising the reactors of the application, the overall peroxide concentration in the peroxide mixture (PM) prior to entering the reactor is 500-1000 mmol/L as determined by iodometric titration.

For example, for any of the reactors of the application or methods comprising the reactors of the application, the overall peroxide concentration in the peroxide mixture (PM) prior to entering the reactor is 600-1000 mmol/L as determined by iodometric titration.

For example, for any of the reactors of the application or methods comprising the reactors of the application, the overall peroxide concentration in the peroxide mixture (PM) prior to entering the reactor is 600-900 mmol/L as determined by iodometric titration.

For example, for any of the reactors of the application or methods comprising the reactors of the application, the overall peroxide concentration in the peroxide mixture (PM) prior to entering the reactor is 700-1000 mmol/L as determined by iodometric titration.

For example, for any of the reactors of the application or methods comprising the reactors of the application, the overall peroxide concentration in the peroxide mixture (PM) prior to entering the reactor is 700-900 mmol/L as determined by iodometric titration.

For example, for any of the reactors of the application or methods comprising the reactors of the application, the overall peroxide concentration in the peroxide mixture (PM) prior to entering the reactor is 700-800 mmol/L as determined by iodometric titration.

For example, for any of the reactors of the application or methods comprising the reactors of the application, the overall peroxide concentration in the peroxide mixture (PM) prior to entering the reactor is about 770 mmol/L as determined by iodometric titration.

For example, for any of the reactors of the application or methods comprising the reactors of the application, the overall peroxide concentration in the peroxide mixture (PM) prior to entering the reactor is 770 mmol/L as determined by iodometric titration.

For example, for any of the reactors of the application or methods comprising the reactors of the application, the overall peroxide concentration in the peroxide mixture (PM) prior to entering the reactor is about 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 mmol/L as determined by iodometric titration.

For example, for any of the reactors of the application or methods comprising the reactors of the application, the overall peroxide concentration in the peroxide mixture (PM) prior to entering the reactor is 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1575, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975 or 2000 mmol/L as determined by iodometric titration.

For example, for any of the reactors of the application or methods comprising the reactors of the application, the overall peroxide concentration in the quenched product solution (QPS) upon exiting the reactor is less than or equal to 200 mmol/L as determined by iodometric titration.

For example, for any of the reactors of the application or methods comprising the reactors of the application, the overall peroxide concentration in the quenched product solution (QPS) upon exiting the reactor is less than or equal to 190 mmol/L as determined by iodometric titration.

For example, for any of the reactors of the application or methods comprising the reactors of the application, the overall peroxide concentration in the quenched product solution (QPS) upon exiting the reactor is less than or equal to 180 mmol/L as determined by iodometric titration.

For example, for any of the reactors of the application or methods comprising the reactors of the application, the overall peroxide concentration in the quenched product solution (QPS) upon exiting the reactor is less than or equal to 170 mmol/L as determined by iodometric titration.

For example, for any of the reactors of the application or methods comprising the reactors of the application, the overall peroxide concentration in the quenched product solution (QPS) upon exiting the reactor is less than or equal to 160 mmol/L as determined by iodometric titration.

For example, for any of the reactors of the application or methods comprising the reactors of the application, the overall peroxide concentration in the quenched product solution (QPS) upon exiting the reactor is less than or equal to 150 mmol/L as determined by iodometric titration.

For example, for any of the reactors of the application or methods comprising the reactors of the application, the overall peroxide concentration in the quenched product solution (QPS) upon exiting the reactor is less than or equal to 140 mmol/L as determined by iodometric titration.

For example, for any of the reactors of the application or methods comprising the reactors of the application, the overall peroxide concentration in the quenched product solution (QPS) upon exiting the reactor is less than or equal to 130 mmol/L as determined by iodometric titration.

For example, for any of the reactors of the application or methods comprising the reactors of the application, the overall peroxide concentration in the quenched product solution (QPS) upon exiting the reactor is less than or equal to 120 mmol/L as determined by iodometric titration.

For example, for any of the reactors of the application or methods comprising the reactors of the application, the overall peroxide concentration in the quenched product solution (QPS) upon exiting the reactor is less than or equal to 110 mmol/L as determined by iodometric titration.

For example, for any of the reactors of the application or methods comprising the reactors of the application, the overall peroxide concentration in the quenched product solution (QPS) upon exiting the reactor is less than or equal to 100 mmol/L as determined by iodometric titration.

For example, for any of the reactors of the application or methods comprising the reactors of the application, the overall peroxide concentration in the quenched product solution (QPS) upon exiting the reactor is less than or equal to 90 mmol/L as determined by iodometric titration.

For example, for any of the reactors of the application or methods comprising the reactors of the application, the overall peroxide concentration in the quenched product solution (QPS) upon exiting the reactor is less than or equal to 80 mmol/L as determined by iodometric titration.

For example, for any of the reactors of the application or methods comprising the reactors of the application, the overall peroxide concentration in the quenched product solution (QPS) upon exiting the reactor is less than or equal to 70 mmol/L as determined by iodometric titration.

For example, for any of the reactors of the application or methods comprising the reactors of the application, the overall peroxide concentration in the quenched product solution (QPS) upon exiting the reactor is less than or equal to 60 mmol/L as determined by iodometric titration.

For example, for any of the reactors of the application or methods comprising the reactors of the application, the overall peroxide concentration in the quenched product solution (QPS) upon exiting the reactor is less than or equal to 60 mmol/L as determined by iodometric titration.

For example, for any of the reactors of the application or methods comprising the reactors of the application, the overall peroxide concentration in the quenched product solution (QPS) upon exiting the reactor is less than or equal to 50 mmol/L as determined by iodometric titration.

For example, for any of the reactors of the application or methods comprising the reactors of the application, the overall peroxide concentration in the quenched product solution (QPS) upon exiting the reactor is less than or equal to 40 mmol/L as determined by iodometric titration.

For example, for any of the reactors of the application or methods comprising the reactors of the application, the overall peroxide concentration in the quenched product solution (QPS) upon exiting the reactor is less than or equal to 30 mmol/L as determined by iodometric titration.

For example, for any of the reactors of the application or methods comprising the reactors of the application, the overall peroxide concentration in the quenched product solution (QPS) upon exiting the reactor is less than or equal to 20 mmol/L as determined by iodometric titration.

For example, for any of the reactors of the application or methods comprising the reactors of the application, the overall peroxide concentration in the quenched product solution (QPS) upon exiting the reactor is less than or equal to 15 mmol/L as determined by iodometric titration.

For example, for any of the reactors of the application or methods comprising the reactors of the application, the overall peroxide concentration in the quenched product solution (QPS) upon exiting the reactor is less than or equal to 10 mmol/L as determined by iodometric titration.

For example, for any of the reactors of the application or methods comprising the reactors of the application, the overall peroxide concentration in the quenched product solution (QPS) upon exiting the reactor is less than or equal to 5 mmol/L as determined by iodometric titration.

For example, for any of the reactors of the application or methods comprising the reactors of the application, the overall peroxide concentration in the quenched product solution (QPS) upon exiting the reactor is less than or equal to 1 mmol/L as determined by iodometric titration.

For example, for any of the reactors of the application or methods comprising the reactors of the application, the reactor has a diameter of 0.25 inches to 10 inches.

For example, for any of the reactors of the application or methods comprising the reactors of the application, the reactor has a diameter of 0.5 inches to 8 inches.

For example, for any of the reactors of the application or methods comprising the reactors of the application, the reactor has a diameter of 1 inch to 6 inches.

For example, for any of the reactors of the application or methods comprising the reactors of the application, the reactor has a diameter of 0.25, 0.5, 0.75, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25 8.5, 8.75, 9, 9.25, 9.5, 9.75 or 10 inches.

For example, for any of the reactors of the application or methods comprising the reactors of the application, the reactor has a length of 5 m to 200 m.

For example, for any of the reactors of the application or methods comprising the reactors of the application, the reactor has a length of 7.5 m to 150 m.

For example, for any of the reactors of the application or methods comprising the reactors of the application, the reactor has a length of 10 m to 100 m.

For example, for any of the reactors of the application or methods comprising the reactors of the application, the reactor has a length of 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 m.

Given the variable nature of the reaction of the peroxide mixtures (PM) with peroxide quenching solution (PQS), residence times in any of the reactors disclosed in this application will be from several minutes to several hours. For example, the peroxide mixture (PM) and/or peroxide quenching solution (PQS) has a residence time in the reactor from 1 to 200 minutes.

For example, for any of the reactors of the application or methods comprising the reactors of the application, the peroxide mixture (PM) and/or peroxide quenching solution (PQS) has a residence time in the reactor from 5 to 120 minutes.

For example, for any of the reactors of the application or methods comprising the reactors of the application, the peroxide mixture (PM) and/or peroxide quenching solution (PQS) has a residence time in the reactor from 5 to 110 minutes.

For example, for any of the reactors of the application or methods comprising the reactors of the application, the peroxide mixture (PM) and/or peroxide quenching solution (PQS) has a residence time in the reactor from 5 to 100 minutes.

For example, for any of the reactors of the application or methods comprising the reactors of the application, the peroxide mixture (PM) and/or peroxide quenching solution (PQS) has a residence time in the reactor from 5 to 90 minutes.

For example, for any of the reactors of the application or methods comprising the reactors of the application, the peroxide mixture (PM) and/or peroxide quenching solution (PQS) has a residence time in the reactor from 5 to 80 minutes.

For example, for any of the reactors of the application or methods comprising the reactors of the application, the peroxide mixture (PM) and/or peroxide quenching solution (PQS) has a residence time in the reactor from 5 to 70 minutes.

For example, for any of the reactors of the application or methods comprising the reactors of the application, the peroxide mixture (PM) and/or peroxide quenching solution (PQS) has a residence time in the reactor from 5 to 60 minutes.

For example, for any of the reactors of the application or methods comprising the reactors of the application, the peroxide mixture (PM) and/or peroxide quenching solution (PQS) has a residence time in the reactor from 5 to 50 minutes.

For example, for any of the reactors of the application or methods comprising the reactors of the application, the peroxide mixture (PM) and/or peroxide quenching solution (PQS) has a residence time in the reactor from 5 to 40 minutes.

For example, for any of the reactors of the application or methods comprising the reactors of the application, the peroxide mixture (PM) and/or peroxide quenching solution (PQS) has a residence time in the reactor from 5 to 30 minutes.

For example, for any of the reactors of the application or methods comprising the reactors of the application, the peroxide mixture (PM) and/or peroxide quenching solution (PQS) has a residence time in the reactor from 5 to 20 minutes.

For example, for any of the reactors of the application or methods comprising the reactors of the application, the peroxide mixture (PM) and/or peroxide quenching solution (PQS) has a residence time in the reactor from 5 to 15 minutes.

For example, for any of the reactors of the application or methods comprising the reactors of the application, the peroxide mixture (PM) and/or peroxide quenching solution (PQS) has a residence time in the reactor from 6 to 12 minutes.

For example, for any of the reactors of the application or methods comprising the reactors of the application, the peroxide mixture (PM) and/or peroxide quenching solution (PQS) has a residence time in the reactor from 8 to 10 minutes.

For example, for any of the reactors of the application or methods comprising the reactors of the application, the peroxide mixture (PM) and/or peroxide quenching solution (PQS) has a residence time in the reactor from 15 to 45 minutes.

For example, for any of the reactors of the application or methods comprising the reactors of the application, the peroxide mixture (PM) and/or peroxide quenching solution (PQS) has a residence time in the reactor from 45 to 90 minutes. For example, for any of the reactors of the application or methods comprising the reactors of the application, the peroxide mixture (PM) and/or peroxide quenching solution (PQS) has a residence time in the reactor of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 minutes.

The output of the quenched product solution (QPS) will have a flow rate, $F_{out}$, which will vary proportionally with the scale of the continuous quenching reaction. For example, the output for the quenched product solution (QPS) has a flow rate out of the reactor, $F_{out}$, of 80 to about 1,000,000 mL/minute.

For example, for any of the reactors of the application or methods comprising the reactors of the application, the output for the quenched product solution (QPS) has a flow rate out of the reactor, $F_{out}$, of 100 to about 500,000 mL/minute.

For example, for any of the reactors of the application or methods comprising the reactors of the application, the output for the quenched product solution (QPS) has a flow rate out of the reactor, $F_{out}$, of 250 to about 250,000 mL/minute.

For example, for any of the reactors of the application or methods comprising the reactors of the application, the output for the quenched product solution (QPS) has a flow rate out of the reactor, $F_{out}$, of 500 to about 100,000 mL/minute.

For example, for any of the reactors of the application or methods comprising the reactors of the application, the output for the quenched product solution (QPS) has a flow rate out of the reactor, $F_{out}$, of about 1,000 to about 100,000 mL/minute.

For example, for any of the reactors of the application or methods comprising the reactors of the application, the output for the quenched product solution (QPS) has a flow rate out of the reactor, $F_{out}$, of about 10,000 to about 100,000 mL/minute.

For example, for any of the reactors of the application or methods comprising the reactors of the application, the output for the quenched product solution (QPS) has a flow rate out of the reactor, $F_{out}$, of about 80 to 100 mL/minute, 90 to 110 mL/minute, 100 to 120 mL/minute, 120 to 140 mL/minute, 130 to 150 mL/minute, 140 to 160 mL/minute, 150 to 170 mL/minute, 160 to 180 mL/minute, 170 to 190 mL/minute, 180 to 200 mL/minute, 500 to 700 mL/minute, 600 to 800 mL/minute, 700 to 900 mL/minute, 800 to 1,000 mL/minute, 900 to 1,100 mL/minute, 1,000 to 1,200 mL/minute, 1,100 to 1,300 mL/minute, 1,400 to 1,600 mL/minute, 1,500 to 1,700 mL/minute, 1,600 to 1,800 mL/minute, 1,700 to 1,900 mL/minute, 1,800 to 2,000 mL/minute, 2,000 to 4,000 mL/minute, 3,000 to 5,000 mL/minute, 4,000 to 6,000 mL/minute, 5,000 to 7,000 mL/minute, 6,000 to 8,000 mL/minute, 7,000 to 9,000 mL/minute, 8,000 to 10,000 mL/minute, 9,000 to 11,000 mL/minute, 10,000 to 12,000 mL/minute, 11,000 to 13,000 mL/minute, 14,000 to 16,000 mL/minute, 15,000 to 17,000 mL/minute, 16,000 to 18,000 mL/minute, 17,000 to 19,000 mL/minute, 18,000 to 20,000 mL/minute, 20,000 to 40,000 mL/minute, 30,000 to 50,000 mL/minute, 40,000 to 60,000 mL/minute, 50,000 to 70,000 mL/minute, 60,000 to 80,000 mL/minute, 70,000 to 90,000 mL/minute, 80,000 to 100,000 mL/minute, 100,000 to 120,000 mL/minute, 110,000 to 130,000 mL/minute, 140,000 to 160,000 mL/minute, 150,000 to 170,000 mL/minute, 160,000 to 180,000 mL/minute, 170,000 to 190,000 mL/minute, 180,000 to 200,000 mL/minute, 200,000 to 400,000 mL/minute, 300,000 to 500,000 mL/minute, 400,000 to 600,000 mL/minute, 500,000 to 700,000 mL/minute, 600,000 to 800,000 mL/minute, 700,000 to 900,000 mL/minute, or 800,000 to 1,000,000 mL/minute.

For example, for any of the reactors of the application or methods comprising the reactors of the application, the output for the quenched product solution (QPS) has a flow rate out of the reactor, $F_{out}$, of about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 500, 1,000, 1,250, 1,500, 1,750, 2,000, 2,250, 2,500, 2,750, 3,000, 3,250, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 20,000, 30,000, 40,000, 50,000, 60,000, 70,000, 80,000, 90,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, or 1,000,000 mL/minute.

For example, for any of the reactors of the application or methods comprising the reactors of the application, the overall pressure in the reactor is about 0.1 psi to 6000 psi.

For example, for any of the reactors of the application or methods comprising the reactors of the application, the overall pressure in the reactor is 0.1 psi to 6000 psi.

For example, for any of the reactors of the application or methods comprising the reactors of the application, the overall pressure in the reactor is 0.5 psi to 6000 psi.

For example, for any of the reactors of the application or methods comprising the reactors of the application, the overall pressure in the reactor is 1 psi to 6000 psi.

For example, for any of the reactors of the application or methods comprising the reactors of the application, the overall pressure in the reactor is 1 psi to 2000 psi.

For example, for any of the reactors of the application or methods comprising the reactors of the application, the overall pressure in the reactor is 1 psi to 1000 psi.

For example, for any of the reactors of the application or methods comprising the reactors of the application, the overall pressure in the reactor is 1 psi to 500 psi.

For example, for any of the reactors of the application or methods comprising the reactors of the application, the overall pressure in the reactor is 1 psi to 200 psi.

For example, for any of the reactors of the application or methods comprising the reactors of the application, the overall pressure in the reactor is 10 psi to 100 psi.

For example, for any of the reactors of the application or methods comprising the reactors of the application, the overall pressure in the reactor is 1 psi to 50 psi.

For example, for any of the reactors of the application or methods comprising the reactors of the application, the overall pressure in the reactor is 0.1 psi to 50 psi.

For example, for any of the reactors of the application or methods comprising the reactors of the application, the overall pressure in the reactor is 0.1 psi to 30 psi.

For example, for any of the reactors of the application or methods comprising the reactors of the application, the overall pressure in the reactor is 0.1 psi to 20 psi.

For example, for any of the reactors of the application or methods comprising the reactors of the application, the overall pressure in the reactor is 0.1 psi to 15 psi.

For example, for any of the reactors of the application or methods comprising the reactors of the application, the overall pressure in the reactor is 0.1 psi to 10 psi.

For example, for any of the reactors of the application or methods comprising the reactors of the application, the overall pressure in the reactor is 0.1 psi to 5 psi.

For example, for any of the reactors of the application or methods comprising the reactors of the application, the overall pressure in the reactor is 0.1 psi to 2 psi.

For example, for any of the reactors of the application or methods comprising the reactors of the application, the overall pressure in the reactor is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.5, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 psi.

For example, for any of the reactors of the application or methods comprising the reactors of the application, the circulatory pump is an electrically powered centrifugal pump.

For example, for any of the reactors of the application or methods comprising the reactors of the application, the heat exchanger is a water bath.

For example, for any of the reactors of the application or methods comprising the reactors of the application, the reactor further comprises one or more static mixers.

For example, for any of the reactors of the application or methods comprising the reactors of the application, the reactor is made of marine grade stainless steel piping.

For example, for any of the reactors of the application or methods comprising the reactors of the application, the reactor is made of nickel-alloy piping.

For example, for any of the reactors of the application or methods comprising the reactors of the application, the piping has Schedule 40 dimensions. Schedule 80 dimensions. or Schedule 160 dimensions.

For example, for any of the reactors of the application or methods comprising the reactors of the application, the peroxide quenching solution (PQS) quenches the peroxide mixture (PM) oxidatively.

For example, for any of the reactors of the application or methods comprising the reactors of the application, the peroxide quenching solution (PQS) comprises nitric acid.

For example, for any of the reactors of the application or methods comprising the reactors of the application, the peroxide quenching solution (PQS) quenches the peroxide mixture (PM) reductively.

For example, for any of the reactors of the application or methods comprising the reactors of the application, the peroxide quenching solution (PQS) comprises thiodiglycol.

For example, for any of the reactors of the application or methods comprising the reactors of the application, the peroxide mixture (PM) is derived from any $C_4$-$C_{50}$ unsaturated material.

For example, for any of the reactors of the application or methods comprising the reactors of the application, the peroxide mixture (PM) is derived from a terpene, fatty acid ester, fatty acid or vegetable oil.

In one embodiment, the peroxide mixture (PM) and the peroxide quenching solution (PQS) are recirculated through the reactor as many times as necessary before collecting the quenched product solution (QPS) from the output. The necessary number of recirculations needed to achieve an acceptable conversion of the peroxide mixture (PM) may be determined by iodometric titration.

This application also pertains to process for the preparation of compound of formula III,

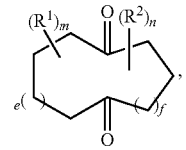

comprising the quenching reaction of an ozonide of formula II,

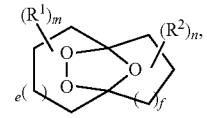

wherein
$R^1$ and $R^2$ are independently selected from $C_1$-$C_{10}$ alkyl, $C_1$-$C_{10}$ hydroxyalkyl, $C_1$-$C_{10}$ haloalkyl and $C_1$-$C_{10}$ alkoxy;
each of e, f, m, and n are independently are independently 0, 1, 2, 3, 4, 5, or 6; and
wherein the quenching reaction is performed in the presence of one or more acids at a temperature of 40° C. to 140° C., wherein the quenching reaction optionally comprises quenching agent.

This application also pertains to process for the preparation of compound of formula III,

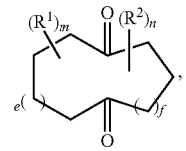

comprising the quenching reaction of an ozonide of formula II,

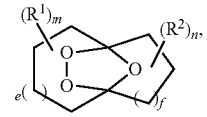

wherein
$R^1$ and $R^2$ are independently selected from $C_1$-$C_{10}$ alkyl, $C_1$-$C_{10}$ hydroxyalkyl, $C_1$-$C_{10}$ haloalkyl and $C_1$-$C_{10}$ alkoxy;
each of e, f, m, and n are independently are independently 0, 1, 2, 3, 4, 5, or 6; and
wherein the quenching reaction is performed in the presence of one or more acids at a temperature of 40° C. to 140° C., wherein the quenching reaction optionally comprises quenching agent;
wherein the ozonide of formula II is prepared from the ozonolysis of a compound of formula I,

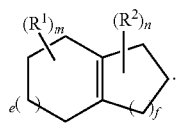

I

In one embodiment, for any of the processes for the preparation of compound of formula III disclosed herein, $R^1$ and $R^2$ are independently selected from $C_1$-$C_6$ alkyl. For example, $R^1$ and $R^2$ are independently selected methyl, ethyl, $C_3$-alkyl, $C_4$-alkyl, $C_5$-alkyl or $C_6$ alkyl.

In one embodiment, for any of the processes for the preparation of compound of formula III disclosed herein, m and n are independently selected from 0, 1 and 2.

For example, m is 0 and n is 0, 1 or 2; m is 1 and n is 0, 1 or 2; m is 2 and n is 0, 1 or 2.

For example, n is 0 and m is 0, 1 or 2; n is 1 and m is 0, 1 or 2; n is 2 and m is 0, 1 or 2.

For example, m is 0 and n is 0.
For example, m is 0 and n is 1.
For example, m is 0 and n is 2.
For example, m is 1 and n is 0.
For example, m is 1 and n is 1.
For example, m is 1 and n is 2.
For example, m is 2 and n is 0.
For example, m is 2 and n is 1.
For example, m is 2 and n is 2.

In one embodiment, for any of the processes for the preparation of compound of formula III disclosed herein, e and f are independently selected from 0, 1, 2, 3, 4, 5, and 6.

For example, e is 0.
For example, e is 1.
For example, e is 2.
For example, e is 3.
For example, e is 4.
For example, e is 5.
For example, e is 6.
For example, f is 0.
For example, f is 1.
For example, f is 2.
For example, f is 3.
For example, f is 4.
For example, f is 5.
For example, f is 6.

In one embodiment, for any of the processes for the preparation of compound of formula III disclosed herein, e and f are independently selected from 0, 1 and 2.

For example, e is 0 and f is 0.
For example, e is 0 and f is 1.
For example, e is 0 and f is 2.
For example, e is 1 and f is 0.
For example, e is 1 and f is 1.
For example, e is 1 and f is 2.
For example, e is 2 and f is 0.
For example, e is 2 and f is 1.
For example, e is 2 and f is 2.

In one embodiment, for any of the processes for the preparation of compound of formula III disclosed herein, the quenching reaction is performed in the presence of one or more acids, wherein the acid is acetic acid, propanoic acid, oxalic acid, hydrochloric acid, or sulfuric acid.

In one embodiment, for any of the processes for the preparation of compound of formula III disclosed herein, the quenching reaction is performed in the presence of one or more acids, wherein the acid is acetic acid.

In one embodiment, for any of the processes for the preparation of compound of formula III disclosed herein, the quenching reaction is performed in the presence of one or more acids, wherein the acid is propanoic acid.

In one embodiment, for any of the processes for the preparation of compound of formula III disclosed herein, the quenching reaction is performed in the presence of one or more acids, wherein the acid is oxalic acid.

In one embodiment, for any of the processes for the preparation of compound of formula III disclosed herein, the quenching reaction is performed in the presence of one or more acids, wherein the acid is hydrochloric acid.

In one embodiment, for any of the processes for the preparation of compound of formula III disclosed herein, the quenching reaction is performed in the presence of one or more acids, wherein the acid is sulfuric acid.

In one embodiment, for any of the processes for the preparation of compound of formula III disclosed herein, the quenching reaction is performed in the presence of one or more acids, wherein the acids are acetic acid and propanoic acid.

In one embodiment, for any of the processes for the preparation of compound of formula III disclosed herein, the quenching reaction is performed in a mixture of acetic and propanoic acid. For example, a 20:1, 19:1, 18:1, 17:1, 16:1, 15:1, 14:1, 13:1, 12:1, 11:1, 10:1, 9:1, 8:1, 7:1, 6:1, 5:1, 4:1, 3.5:1, 3:1, 2.5:1, 2:1, 1.5:1, or 1:1 mixture of acetic acid in propanoic acid (volume/volume) or propanoic acid in acetic acid (volume/volume).

In one embodiment, for any of the processes for the preparation of compound of formula III disclosed herein, the quenching reaction is performed at a temperature of 40° C. to 140° C., 50° C. to 140° C., 60° C. to 140° C., 60° C. to 130° C., 70° C. to 130° C., 75° C. to 125° C., 80° C. to 120° C., 80° C. to 115° C., 80° C. to 110° C. or 85° C. to 105° C.

In one embodiment, for any of the processes for the preparation of compound of formula III disclosed herein, the quenching reaction is performed at a temperature of 40° C., 45° C., 50° C., 55° C., 60° C., 65° C., 70° C., 75° C., 80° C., 85° C., 90° C., 95° C., 100° C., 110° C., 115° C., 120° C., 125° C., 130° C., 135° C., or 140° C.

In one embodiment, for any of the processes for the preparation of compound of formula III disclosed herein, the quenching reaction does not comprise a quenching agent.

In one embodiment, for any of the processes for the preparation of compound of formula III disclosed herein, the quenching reaction comprises a quenching agent In one embodiment, for any of the processes for the preparation of compound of formula III disclosed herein, wherein the quenching reaction comprises a quenching agent, wherein the quenching reagent is selected from bisulfite, triphenyl phosphine, dimethyl sulfide, thiodiglycol, and catalytic hydrogenation.

For example, the quenching reagent is bisulfite.
For example, the quenching reagent is triphenyl phosphine.
For example, the quenching reagent is dimethyl sulfide.
For example, the quenching reagent is thiodiglycol.
For example, the quenching reagent is catalytic hydrogenation.

In one embodiment, for any of the processes for the preparation of compound of formula III disclosed herein, the molar ratio of the quenching reagent to the ozonide of formula II is 0.25:1, 0.5:1, 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

For example, the molar ratio of the quenching reagent to the ozonide of formula II is 0.5:1.

For example, the molar ratio of the quenching reagent to the ozonide of formula II is 1:1.

For example, the molar ratio of the quenching reagent to the ozonide of formula II is 1.5:1.

For example, the molar ratio of the quenching reagent to the ozonide of formula II is 2:1.

This application also pertains to process for the preparation of compound IIIa,

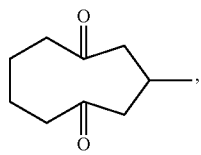

comprising the quenching reaction of an ozonide IIa,

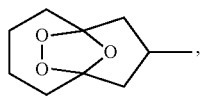

wherein
wherein the quenching reaction is performed in acetic acid, propanoic acid, or a mixture thereof at a temperature of 80° C. to 140° C., wherein the quenching reaction optionally comprises quenching agent.

This application also pertains to process for the preparation of compound IIIa,

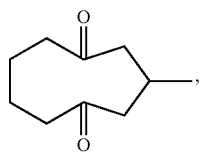

comprising the quenching reaction of an ozonide IIa,

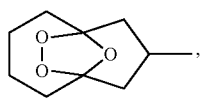

wherein the quenching reaction is performed in the presence of one or more acids at a temperature of 80° C. to 140° C., wherein the quenching reaction optionally comprises quenching agent;
wherein the ozonide IIa is prepared from the ozonolysis of compound Ia,

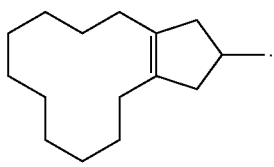 [SMILES: CC1CC2=C(CCCCCCCCCC2)C1]

In one embodiment, for any of the processes for the preparation of compound IIIa disclosed herein, the quenching reaction is performed in the presence of one or more acids, wherein the acid is acetic acid, propanoic acid, oxalic acid, hydrochloric acid, or sulfuric acid.

In one embodiment, for any of the processes for the preparation of compound IIIa disclosed herein, the quenching reaction is performed in the presence of one or more acids, wherein the acid is acetic acid.

In one embodiment, for any of the processes for the preparation of compound IIIa disclosed herein, the quenching reaction is performed in the presence of one or more acids, wherein the acid is propanoic acid.

In one embodiment, for any of the processes for the preparation of compound IIIa disclosed herein, the quenching reaction is performed in the presence of one or more acids, wherein the acid is oxalic acid.

In one embodiment, for any of the processes for the preparation of compound IIIa disclosed herein, the quenching reaction is performed in the presence of one or more acids, wherein the acid is hydrochloric acid.

In one embodiment, for any of the processes for the preparation of compound IIIa disclosed herein, the quenching reaction is performed in the presence of one or more acids, wherein the acid is sulfuric acid.

In one embodiment, for any of the processes for the preparation of compound IIIa disclosed herein, the quenching reaction is performed in the presence of one or more acids, wherein the acids are acetic acid and propanoic acid.

In one embodiment, for any of the processes disclosed herein for the preparation of a compound of formula III, e.g., compound IIIa, the quenching reaction is performed in acetic acid.

In one embodiment, for any of the processes disclosed herein for the preparation of a compound of formula III, e.g., compound IIIa, the quenching reaction is performed in propanoic acid.

In one embodiment, for any of the processes disclosed herein for the preparation of a compound of formula III, e.g., compound IIIa, the quenching reaction is performed in a mixture of acetic and propanoic acid. For example, a 20:1, 19:1, 18:1, 17:1, 16:1, 15:1, 14:1, 13:1, 12:1, 11:1, 10:1, 9:1, 8:1, 7:1, 6:1, 5:1, 4:1, 3.5:1, 3:1, 2.5:1, 2:1, 1.5:1, or 1:1 mixture of acetic acid:propanoic acid (volume/volume) or propanoic acid:acetic acid (volume/volume).

In one embodiment, for any of the processes for the preparation of compound IIIa disclosed herein, the quenching reaction is performed at a temperature of 80° C. to 130° C., 80° C. to 120° C., 85° C. to 120° C., 90° C. to 120° C., 95° C. to 120° C., 95° C. to 125° C., 95° C. to 115° C., 80° C. to 90° C., 90° C. to 100° C., 100° C. to 110° C., or 110° C. to 120° C.

In one embodiment, for any of the processes for the preparation of compound IIIa disclosed herein, the quenching reaction is performed at a temperature of 80° C., 85° C., 90° C., 95° C., 100° C., 110° C., 115° C., 120° C., 125° C., 130° C., 135° C., or 140° C.

In one embodiment, for any of the processes for the preparation of compound IIIa disclosed herein, the quenching reaction does not comprise a quenching agent.

In one embodiment, for any of the processes for the preparation of compound IIIa disclosed herein, the quenching reaction comprises a quenching agent.

In one embodiment, for any of the processes for the preparation of compound IIIa disclosed herein, wherein the quenching reaction comprises a quenching agent, wherein the quenching reagent is selected from bisulfite, triphenyl phosphine, dimethyl sulfide, thiodiglycol, and catalytic hydrogenation.

For example, the quenching reagent is bisulfite.

For example, the quenching reagent is triphenyl phosphine.

For example, the quenching reagent is dimethyl sulfide.

For example, the quenching reagent is thiodiglycol.

For example, the quenching reagent is catalytic hydrogenation.

In one embodiment, for any of the processes for the preparation of compound IIIa disclosed herein, the molar ratio of the quenching reagent to ozonide IIa is 0.25:1, 0.5:1, 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, or 5:1.

For example, the molar ratio of the quenching reagent to ozonide IIa is 0.5:1.

For example, the molar ratio of the quenching reagent to ozonide IIa is 1:1.

For example, the molar ratio of the quenching reagent to ozonide IIa is 1.5:1.

For example, the molar ratio of the quenching reagent to ozonide IIa is 2:1.

The transformation of ozonide IIa to diketone IIIa is known and has been reported in the literature (*Helvetica Chimica Acta* 2009, Vol. 92, p. 1782-1798; *Helvetica Chimica Acta* 1967, Vol. 50, p. 705-708; U.S. Pat. No. 3,778,483). In the most recent report, the formation of diketone product IIIa was accomplished in an ozonolysis reaction in ethanol under cryogenic conditions (−78° C.), followed by catalytic hydrogenation using palladium on carbon. However, only a 67% yield of the diketone product was reported under these conditions due to insufficient quenching of ozonide intermediate. Following ozonolysis of this particular bicyclic olefin Ia, there is often 30-60% of a highly stable ozonide IIa that remains even after quenching with standard reducing agents including bisulfite, triphenyl phosphine, dimethyl sulfide, thiodiglycol, and catalytic hydrogenation. Even at non-cryogenic temperatures, i.e., temperatures greater than −78° C. and up to ambient temperature, highly stable ozonide IIa remains unreacted.

It was surreptitiously observed that an acid could be used to digest this ozonide at elevated temperatures, specifically at temperatures greater than 60° C., for example, between 80° C. and 110° C. The acid or acids employed in the quenching reaction may be used in catalytic, sub-stoichiometric, or excess amounts compared to the ozonide. The acid or acids may also be used as the solvent of the quenching reaction.

The acidic properties of the solvent and the high temperature of the quenching reaction are responsible for the improved yield. For example, the yields of the desired diketone IIIa improved significantly under these optimized conditions (80-100%) compared to the yields reported in the art (40-70%).

The quenching reaction may use a solvent in addition to the one or more acids. For example, solvents may be selected from the group consisting of: alcohols (e.g., ethanol, iso-propanol, n-butanol), ethers (e.g., methyl tert-butyl ether, diethyl ether, tetrahydrofuran), halogenated hydrocarbons (e.g., dichloromethane, 1,2-dichloroethane), water, aromatics (e.g., benzene, phenol, toluene), and mixtures thereof. These examples are not intended to be limiting. In one embodiment, the solvent is the acid or acids used in the quenching reaction, e.g., acetic acid, propanoic acid, or a mixture of acetic and propanoic acid. In one embodiment, in addition to one or more acids and heat, the quenching reaction uses a solvent which includes n-butanol, water, and combinations thereof, for purposes of digesting the cyclic ozonide.

The process disclosed herein for quenching ozonide IIa to diketone IIIa has advantages over the prior art. Importantly, the isolated yields of diketone IIIa are markedly improved over the known quenching conditions. Related to the improved isolated yield of diketone IIIa, the conversion of ozonide IIa is complete or nearly complete under the optimized conditions. This improved conversion results in the isolation of diketone IIIa in high purity. Secondly, the optimized conditions avoid the use of the cryogenic quenching conditions reported in the prior art, which is particularly advantageous because employing cryogenic conditions on a large scale is both labor-intensive and costly.

Ozonides are known in the art to be highly reactive compounds. A skilled person would be well aware of their reactivity and would avoid heating ozonides at elevated temperature during quenching reactions because of safety concerns. These optimized quenching conditions unexpectedly solve an established problem in the art (formation of diketone IIIa) using an inventive process, i.e., heating notoriously unstable ozonides at high temperatures (between 80° C. and 110° C.).

An optimized subset of conditions for the ozonide quenching reaction included using one or more acids at a temperature of about 90° C., in the presence of a quenching agent (e.g., bisulfite, triphenyl phosphine, dimethyl sulfide, thiodiglycol, and catalytic hydrogenation). These conditions result in high yields of diketone IIIa in high purity in just under 3 hrs. in a batch condition. It was found that even less reaction time was necessary using a continuous reactor. Other acids, immobilized or otherwise, can also be used, including, without limitation.

The critical features for the quenching reaction of a stable ozonide (e.g., ozonide IIa) are acid and elevated temperature, and these conditions may be applied to a wide array of stable ozonides.

The recirculating flow-through reactors and processes described herein for may be used for the continuous quenching of a peroxide mixture (PM), wherein the peroxide mixture (PM) is derived from any reaction, method, or process that provides a reactive oxygen species intermediate. For example, the reactive oxygen species intermediate may be formed during an ozonolysis reaction. For example, the reactive oxygen species intermediate may be formed during a Baeyer-Villiger reaction. For example, the reactive oxygen species intermediate may be formed during a Dakin reaction. For example, the reactive oxygen species intermediate may be formed during a hydroboration reaction. For example, the reactive oxygen species intermediate may be formed during an epoxidation reaction.

The list of ozonides that may be quenched in any of the methods, processes, or reactors described herein includes both primary and secondary ozonides resulting from $C_4$-$C_{50}$ mono-, di-, or tri-unsaturated alkanes.

For example, the list of ozonides includes, without limitation, both primary and secondary ozonides resulting from the reaction of ozone with monoterpenes, sesquiterpenes, diterpenes, vegetable oils, fatty acids, fatty acid esters, cyclic olefins, linear alkyl olefins, quinolones, or naphthalenes.

Monoterpenes include any compound with the base formula $C_{10}H_{16}$ and biochemically modified variants of monoterpenes arising from oxidation and/or rearrangement, i.e., monoterpenoids. These include but are not limited to myrcene, pinene, carene, limonene, camphor, borneol, eucalyptol, etc.

Sesquiterpenes include any compound with the base formula $C_{15}H_{24}$ and biochemically modified variants of sesquiterpenes arising from oxidation and/or rearrangement, i.e., sesquiterpenoids. These include but are not limited to zingiberene, humulene, caryophyllene, longifolene, etc.

Diterpenes include any compound with the base formula $C_{20}H_{32}$ and biochemically modified variants of diterpenes arising from oxidation and/or rearrangement, i.e., diterpenoids. These include but are not limited to cembrene, scalrene, taxadiene, stemarene, phytol, retinol, etc.

For example, a list of reductive quenching reagents includes bisulfite salts, sulfite salts, phosphites, phosphines, dimethyl sulfide, thiodiglycol, rongalite, thiols, thiosulfate, borohydrides, aluminum hydrides, hydrogen in the presence of a metal catalyst (e.g., Pd, Ni, or Pt), or any combination thereof.

For example, a list of oxidative quenching reagents includes hydrogen peroxide, peracetate, peracetic acid, persulfate, percarbonate, oxygen, manganese, manganese acetate, manganese on sold support, nitric acid, sulfuric acid, chlorates, bromates, perborates, chlorites, bromites, nitrates, nitrous oxide, or any combination thereof.

For example, the reactors of the disclosure (and methods comprising said reactors) include those where each of the variables defined herein, including reactor dimensions (e.g. length and width), location of entry ports, residence time for peroxide mixtures (PM) and peroxide quenching solutions (QPS) in the reactor, reactor temperatures, flow rate, $F_{out}$, of the quenched ozonide from the reactor via the outlet port, reactor pressure, contraction and/or expansion of the reactor by the addition of valves and additional piping, presence or absence static mixers, etc., can be combined with any of the other variables disclosed herein.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

In one embodiment, enzymes such as a catalase may be used to quench peroxide mixtures (PM) in the reactors described herein. See U.S. Patent Application Publication No. 2013/0078685.

In one embodiment, the reactors described herein and methods comprising the same may be coupled with reactors and/or methods for continuous ozonolysis reactions. For example, the reactors for the continuous ozonolysis reaction may have one or more microchannels. See U.S. Pat. No. 7,825,277. In another example, the reactors for the continuous ozonolysis reaction may be falling film reactors. See PCT Publication No. WO 2015196019.

It should be appreciated that each peroxide mixture (PM) and peroxide quenching solution (QPS, which contains one or more quenching reagent) will react at different rates, which means that the time for the reaction to go to completion, i.e., the time required for the peroxide mixture (PM) to be converted to the quenched product solution (QPS) will also vary.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Further, it should be appreciated that the embodiments described herein may be operated manually and/or automatically. A computer may be used to automate any of the embodiments described herein.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The term "ozonide" or "ozonide mixture" refers to the unstable and reactive cyclic intermediates in the reaction of ozone with an unsaturated compound and mixtures thereof. The term "ozonide" or "ozonide mixture" includes primary ozonide, secondary ozonides, and mixtures thereof.

The term "peroxide" or "peroxide mixture" refers to any species or intermediate that contains an oxygen-oxygen single bond or the peroxide anion. Peroxides or peroxide mixtures include ozonides and ozonide mixtures, in addition to other reactive species falling under the definition.

The reactors of the application, or methods comprising the reactors of the application, optionally comprise a heat exchanger, which is employed to maintain the temperature inside the reactor. For example, for any of the reactors of the application or methods comprising the reactors of the application, the heat exchanger can be a brazed plate heat exchanger, a fusion-bonded plate heat exchanger, a gasketed plate-and-frame heat exchanger, a welded plate-and-shell heat exchanger, an welded plate-and-block heat exchanger, a printed circuit heat exchanger, a welded spiral heat exchanger, or welded plate-and-frame heat exchanger.

In one aspect, the heat exchanger (HE) is an Alfa Laval heat exchanger (http://www.alfalaval.us/). For example, the heat exchanger (HE) is an Alfa Laval brazed plate heat exchanger, an Alfa Laval fusion-bonded plate heat exchanger, an Alfa Laval gasketed plate-and-frame heat exchanger, an Alfa Laval welded plate-and-shell heat exchanger, an Alfa Laval welded plate-and-block heat exchanger, an Alfa Laval printed circuit heat exchanger, an Alfa Laval welded spiral heat exchanger, or an Alfa Laval welded plate-and-frame heat exchanger.

In one aspect, for any of the reactors of the application, or methods comprising the reactors of the application, the heat exchanger (HE) is the reactor. For example, in one embodiment, an Alfa Laval gasketed plate-and-frame heat exchanger is the reactor, further comprising any of the features described herein.

The term "acid," as used herein, refers to mineral acids, e.g., hydrofluoric acid, hydrochloric acid, hydrobromic acid, hydroiodic acid, hypochlorous acid, chlorus acid, chloric acid, perchloric acid; sulfuric acid, nitric acid, phosphoric acid, chromic acid, boric acid; sulfonic acids, i.e., a compound with a —S(O)$_2$OH moiety, including, without limitation, methanesulfonic acid, ethanesulfonic acid, benzenesulfonic acid, p-toluenesulfonic acid, trifluoromethanesulfonic acid, sulfonated polystyrene; carboxylic acids, i.e., a compound with a —C(O)OH moiety, including, without limitation, acetic acid, propanoic acid, citric acid, formic acid, gluconic acid, lactic acid, oxalic acid, tartaric acid, butanoic acid; halogenated carboxylic acids, i.e., a compound with a —C(O)OH moiety and containing at least one halogen, including, without limitation, chloroacetic acid, trifluoroacetic acid, and the like; vinylogous carboxylic acids, i.e., a compound with a —C(O)—C=C—OH— moiety, including, without limitation, ascorbic acid; nucleic acids; and amino acids.

The term "$C_1$-$C_{10}$ alkyl," as used herein, refers to a straight chain or branched alkane that has 1, 2, 3, 4, 5, 6, 7, 8, 9 or 10 carbons. Examples include methyl, ethyl, n-propyl, iso-propyl, n-butyl, i-butyl, s-butyl, n-pentyl, i-pentyl, n-hexyl, heptyl, octyl, nonyl, and decyl. In certain embodiments, one or more of the carbon atoms in any $C_1$-$C_{10}$ alkyl group may be replaced with an O atom or an NH group. In one embodiment, one of the carbon atoms in any $C_1$-$C_{10}$ alkyl group may be replaced with an O atom or an NH group. In one embodiment, two of the carbon atoms in any $C_1$-$C_{10}$ alkyl group may be replaced with an O atom or an NH group. In one embodiment, three of the carbon atoms in any $C_1$-$C_{10}$ alkyl group may be replaced with an O atom or an NH group. In one embodiment, four of the carbon atoms in any $C_1$-$C_{10}$ alkyl group may be replaced with an O atom or an NH group.

The term "$C_1$-$C_{10}$ hydroxyalkyl," as used herein, refers to a $C_1$-$C_{10}$ alkyl substituted by one or more hydroxyl group (—OH). In one embodiment, a $C_1$-$C_{10}$ hydroxyalkyl group is substituted by one —OH. In one embodiment, a $C_1$-$C_{10}$ hydroxyalkyl group is substituted by two —OH. In one embodiment, a $C_1$-$C_{10}$ hydroxyalkyl group is substituted by three —OH. In one embodiment, a $C_1$-$C_{10}$ hydroxyalkyl group is substituted by four —OH.

The term "$C_1$-$C_{10}$ haloalkyl," as used herein, refers to a $C_1$-$C_{10}$ alkyl substituted by one or more halogens (halo). $C_1$-$C_{10}$ haloalkyl includes perhalogenated alkyl groups such as —$CF_3$, —$CCl_2CCl_3$, and the like.

The term "halo" as used herein, refers to a halogen atom, including fluoro (F), chloro (Cl), bromo (Br), and iodo (I).

The term "$C_1$-$C_{10}$ alkoxy," as used herein, refers to an —O—$C_1$-$C_{10}$ alkyl group.

Iodometric titration may be used to determine the concentration of peroxide species in the peroxide mixture (PM) or quenched product solution (QPS).

The term "about," as used herein, and unless explicitly stated otherwise, refers to a recited value +/−10%, +/−5%, +/−2.5%, +/−1%, or +/−0.5%. For example, "about" may refer to a recited value +/−5%.

When used referring to any of the reactors described herein, the terms "diameter" and "inner diameter" should be interpreted as equivalent and interchangeable, unless explicitly indicated otherwise.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

The following working example is illustrative of the reactors disclosed herein. It is not intended to be limiting and it will be readily understood by one of skill in the art that other reactors may be utilized.

Example 1—Continuous Quenching

A recirculating flow-through reactor for the continuous quenching of a peroxide mixture (PM), designed to have a 1.08 L loop capacity made from ½" OD (outer diameter) and ⅜" ID (inner diameter) stainless steel tubing arranged in a coil is placed in line with a continuous ozonolysis operation from a falling film tube reactor system wherein oleic acid is being ozonolyzed. The reactor is kept at room temperature in a water bath and is equipped with two inputs: one input for the ozonolyzed product stream, i.e., peroxide mixture (PM), coming from the falling film reactor, and one input for the peroxide quenching solution (PQS). An additional outlet is provided for full or partially quenched product solution (QPS) fluid exiting the reactor. A circulating pump (CP) rated at 7 gal/min is placed in line within the coil loop to provide continuous mixing and circulation. The reactor is primed with 1.0 L of acetic acid.

For the ozonolysis operation, 1 part commercially available high oleic fatty acid (~77% oleic acid as a mixture in other $C_{14}$-$C_{18}$ fatty acids) is mixed with 2 parts acetic acid by volume for a total of 2.4 L of fatty acid mixture. This material is passed through 5.1 m of falling film reactor tube in a concurrent flow at 80 ml/min liquid flowrate. The material leaving the ozonolysis reactor is deemed to be >99% converted and possessed a peroxide value of 770 mmol/L as determined by iodometric titration.

This peroxide mixture (PM) is flowed at the same rate (80 mL/min) into the quenching conduit via the first input. Into the second input is pumped a 20% (by vol.) solution of thiodiglycol in acetic acid at a rate of 40 L/min (1.3 L dosed in total). A continuous volume is maintained within the reactor with an estimated 120 mL/min of quenched or partially quenched ozonide (QPS) leaving the reactor via the output. The calculated residence time for the peroxide mixture (PM) and peroxide quenching solution (PQS) in the reactor is 8-10 minutes. After passing through the reactor the quenched product solution (QPS) is determined to have a peroxide concentration of 60 mmol/L, representing >80% reduction compared to the material leaving the ozonolysis reactor.

Example 2—Ozonolysis of a Bicyclic Olefin and Characterization of its Stable Ozonide Product 2-methyl-2,3,4,5,6,7,8,9,10,11,12,13-dodecahydro-1H-cyclopenta[12]annulene (compound Ia) (100 g, 454 mmol) is combined with 100 g of water and 100 g of acetic acid and the mixture is cooled down to 15° C. with rapid stirring in a jacketed glass reactor equipped with overhead stirrer and controlled gas diffusion. 8-9% by wt. ozone in oxygen gas is then diffused into the mixture at a flow rate of 3 L/min. Gas is introduced for 180 minutes until starting material is completely consumed, ensuring that the reaction did not exceed 22° C. The mixture is then purged with $N_2$ and treated with aqueous $Na_2SO_3$/$NaHSO_3$ solution (125 g/125 g in 1 L) until the KI-starch strip showed negative. Methyl tert-butyl ether (MTBE, 250 mL×3) is used to extract the mixture, which is subsequently washed with aqueous $Na_2CO_3$ (10% w/v) until the emulsion tested for a pH=8. The organic phase is then dried with $Na_2SO_4$, filtered and evaporated to give 110 g of crude product as an off-white solid as a ~1:1 mixture of 3-methylcyclononane-1,5-dione (compound IIIa) and stable ozonide IIa.

The stable ozonide compound IIa is then isolated using column chromatography, where 2 products with similar elution times are isolated, likely a mixture of two conformers of stable ozonide compound IIa. This is consistent with the $^{13}C$ NMR spectrum of the stable ozonide compound IIa, where two peaks at 109 ppm and 110 ppm represent the carbons in the ozonide ring (FIG. 7).

Example 3—Conversion of a Stable Ozonide to a Diketone 20 g of the stable ozonide compound IIa mixture is treated with 50% acetic acid in water (v/v, 100 mL) at 100° C. for 4 hours. The reaction is monitored by TLC until all product has been converted to the desired material. Water (800 mL) is then added and an off-white solid precipitated after the mixture is cooled down to room temperature. The mixture is filtered and the filtration cake is washed with water. The off-white solid is dissolved in MTBE (250 mL) and washed with aqueous $Na_2CO_3$ (10%) until the pH was 8 to remove any trace acetic acid. The organic phase is again dried with $Na_2SO_4$, then filtered and concentrated to give the crude product 18.7 g as an off-white solid containing greater than 85% diketone. No ozonide is present in the crude product, as determined by NMR, TLC, or iodometric titration.

Further experimentation reveals that the quenching reaction of stable ozonide IIa can be accelerated by increasing acid concentration and/or the temperature of the quenching reaction.

What is claimed is:

1. A reactor for the continuous quenching of a peroxide mixture (PM), wherein said reactor is either a single-pass flow-through reactor or a recirculating flow-through reactor, said reactor comprising:
   (a) either (1) a single input for both a peroxide mixture (PM) and a peroxide quenching solution (PQS), or (2) a first input for a PM and a second input for a PQS;
   (b) an output for a quenched product solution (QPS);
   (c) a heat exchanger (HE); and
   (d) optionally, a circulatory pump (CP);
   the output for the quenched product solution (QPS) has a flow rate out of the reactor, $F_{out}$, of 80 to about 1,000,000 mL/minute, and wherein the overall pressure in the reactor is 1 psi to 6000 psi, and wherein the heat exchanger maintains the reactor temperature at −78° C. to 300° C.;
   wherein the reactor is placed in line with a continuous ozonolysis operation from a tubular falling film reactor system with one or multiple tubes wherein the combined ozone and carrier gas flow is co-current; and wherein the reactor is designed to provide an overall peroxide concentration in the quenched product solution (QPS) upon exiting the reactor of less than or equal to 100 mmol/L as determined by iodometric titration when the overall peroxide concentration in the peroxide mixture (PM) prior to entering the reactor is 500 to 2000 mmol/L as determined by iodometric titration.

2. The reactor of claim 1, wherein the reactor is a single-pass flow-through reactor and the reactor further comprises:
a second single-pass flow-through reactor connected to the first single-pass flow-through reactor, said second reactor optionally comprising a circulatory pump (CP), heat exchanger (HE), or both.

3. The reactor of claim 1, wherein the reactor is a single pass-flow through reactor.

4. The reactor of claim 1, wherein the reactor is a recirculating flow-through reactor.

5. The reactor of claim 4, wherein the reactor has
a first input for a peroxide mixture (PM); and a
a second input for a peroxide quenching solution (PQS).

6. The reactor of claim 1, wherein the reactor has a diameter of 0.25 inches to 10 inches.

7. The reactor of claim 1, wherein the reactor has a length of 5 m to 200 m.

8. The reactor of claim 1, wherein the reactor is designed to provide the peroxide mixture (PM) with a residence time in the reactor of from 1 to 200 minutes.

9. The reactor of claim 1, wherein the heat exchanger (HE) maintains the temperature in the reactor at −40° C. to 150° C.

10. The reactor of claim 1, wherein the reactor is designed to provide that the peroxide quenching solution (PQS) quenches the peroxide mixture (PM) oxidatively.

11. The reactor of claim 1, wherein the reactor is designed to provide that the peroxide quenching solution (PQS) quenches the peroxide mixture (PM) reductively.

12. The reactor of claim 4, wherein the reactor is designed to provide that the peroxide mixture (PM) and the peroxide quenching solution (PQS) are recirculated through the reactor 1, 2, 3, or 4 times before collecting the quenched product solution (PQS) from the output.

13. A method of continuously quenching a peroxide mixture (PM) in a reactor according to claim 1.

14. A method of continuously quenching a peroxide mixture (PM) in a reactor according to claim 4.

15. The method of claim 13, wherein the peroxide mixture (PM) is derived from any $C_4$-$C_{50}$ unsaturated material.

16. The method of claim 13, wherein the peroxide mixture (PM) is derived from a terpene, or a fatty acid ester, or a fatty acid, or a vegetable oil.

17. A method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) and a peroxide quenching solution (PQS) into a peroxide mixture (PM) and peroxide quenching solution (PQS) feeding chamber;

(e) feeding the peroxide mixture (PM) and peroxide quenching solution (PQS) into a reactor according to claim 1.

18. A method of performing ozonolysis or ozone-based oxidation on a liquid or emulsified $C_4$-$C_{50}$ unsaturated material with a gaseous reagent comprising ozone and one or more carrier gases to generate a peroxide mixture (PM), followed by the continuous quenching of the peroxide mixture (PM), comprising:

(a) feeding the liquid or emulsified $C_4$-$C_{50}$ unsaturated material from a common liquid or emulsified $C_4$-$C_{50}$ unsaturated material feeding chamber that is maintained completely full through annular slots and into a plurality of parallel and substantially identical tubes, as to form a liquid or emulsified reagent film comprising the $C_4$-$C_{50}$ unsaturated material on the internal surface of each tube;

(b) feeding the gaseous reagent through the annular slots and into the tubes from a gaseous reagent feeding chamber to generate a peroxide mixture (PM), the feeding pressure of the gaseous reagent being substantially the same as the pressure loss from the gaseous reagent flow-through the tubes containing the liquid or emulsified reagent film comprising the $C_4$-$C_{50}$ unsaturated material, but less than the feeding pressure of the liquid or emulsified $C_4$-$C_{50}$ unsaturated material;

(c) cooling the tubes by flowing a liquid coolant through a housing surrounding the tubes;

(d) feeding the peroxide mixture (PM) into a reactor according to claim 4.

* * * * *